(12) United States Patent
Irsch et al.

(10) Patent No.: US 9,713,423 B2
(45) Date of Patent: Jul. 25, 2017

(54) APPARATUS AND METHOD FOR MINIMIZING THE INFLUENCE OF CORNEAL BIREFRINGENCE ON THE ANALYSIS OF EYE FIXATION AND FOCUS USING RETINAL BIREFRINGENCE SCANNING

(71) Applicant: THE JOHNS HOPKINS UNIVERSITY, Baltimore, MD (US)

(72) Inventors: Kristina Irsch, Baltimore, MD (US); David L. Guyton, Baltimore, MD (US); Boris I. Gramatikov, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/776,763

(22) PCT Filed: Mar. 17, 2014

(86) PCT No.: PCT/US2014/030139
§ 371 (c)(1),
(2) Date: Sep. 15, 2015

(87) PCT Pub. No.: WO2014/145383
PCT Pub. Date: Sep. 18, 2014

(65) Prior Publication Data
US 2016/0038025 A1 Feb. 11, 2016

Related U.S. Application Data

(60) Provisional application No. 61/793,350, filed on Mar. 15, 2013.

(51) Int. Cl.
*A61B 3/10* (2006.01)
*A61B 3/00* (2006.01)
(Continued)

(52) U.S. Cl.
CPC .............. *A61B 3/12* (2013.01); *A61B 3/0025* (2013.01); *A61B 3/0091* (2013.01); *A61B 3/10* (2013.01);
(Continued)

(58) Field of Classification Search
USPC .................................................. 351/200–246
See application file for complete search history.

(56) References Cited

U.S. PATENT DOCUMENTS 6,322,554 B1 11/2001 Tomita
7,513,619 B2 4/2009 Lacombe et al.
(Continued)

*Primary Examiner* — Mohammed Hasan
(74) *Attorney, Agent, or Firm* — Johns Hopkins Technology Ventures

(57) ABSTRACT

The present invention provides apparatus and methods for detecting fixation of an eye of a subject on a target. The methods provide for optimization of parameters of the spinning half wave plate and the fixed wave plate in the retinal birefringence scanning (RBS) design to enable uses of the "spinning artifact" frequency component. Frequency of the "spinning artifact" component is determined by half wave plate rotation speed and direction. Amplitude is determined by interaction of the spinning half wave plate with any retardance encountered in the double-pass optics such as the fixed wave plate, corneal birefringence, and small amount of retinal birefringence. With optimum selection of fractional spinning frequency of the half wave plate, and the orientation/retardance of the fixed wave plate, the "spinning artifact" frequency component is essentially independent of fixation direction and is also essentially independent of the normal range of corneal birefringence.

26 Claims, 13 Drawing Sheets

(51) Int. Cl.
*A61B 3/12* (2006.01)
*A61B 3/103* (2006.01)
*G02B 5/30* (2006.01)
*G02B 27/14* (2006.01)
*G02B 27/28* (2006.01)

(52) U.S. Cl.
CPC ............ *A61B 3/103* (2013.01); *G02B 5/3083* (2013.01); *G02B 27/141* (2013.01); *G02B 27/283* (2013.01)

(56) References Cited

U.S. PATENT DOCUMENTS

| | | |
|---|---|---|
| 2009/0310083 A1 | 12/2009 | Campbell et al. |
| 2009/0316111 A1* | 12/2009 | Hunter ............... A61B 3/10 351/201 |
| 2012/0229768 A1* | 9/2012 | Gramatikov ......... A61B 3/113 351/215 |

* cited by examiner

APPARATUS AND METHOD FOR MINIMIZING THE INFLUENCE OF CORNEAL BIREFRINGENCE ON THE ANALYSIS OF EYE FIXATION AND FOCUS USING RETINAL BIREFRINGENCE SCANNING

CROSS-REFERENCE TO RELATED APPLICATIONS

This application is a 35 U.S.C. §371 U.S. national entry of International Application PCT/US2014/030139, having an international filing date of Mar. 17, 2014, which claims the benefit of U.S. Provisional Application No. 61/793,350, filed Mar. 15, 2013, the content of each of the aforementioned applications is herein incorporated by reference in their entirety.

BACKGROUND OF THE INVENTION

The fovea is a highly specialized retinal region that allows a normal visual system to attain better than 20/20 visual acuity. When an individual looks at an object, that object is imaged onto the fovea of the eye. The fovea is surrounded by a uniquely arranged radial pattern of birefringent Henle fibers, fibers that change the state of polarization of transmitted light. The birefringence of these Henle fibers has been exploited to detect true foveal fixation of an eye, by means of retinal birefringence scanning (RBS). In RBS, a spot of polarized near-infrared light is scanned on the retina, most simply in a circle with a fixation point in the center, and the changes in the polarization of light returning from the eye are analyzed to detect the projection into space of the Henle fibers surrounding the fovea.

Due to the radially symmetric arrangement of the birefringent Henle fibers surrounding the fovea, a characteristic frequency (or more than one frequency, depending on the opto-mechanical design) appears in the obtained periodic signal when the scan is exactly centered on the fovea, indicating central fixation. Thus, by analyzing the generated frequencies in the obtained RBS signal, for example by means of the Fast Fourier Transform (FFT), the goodness of eye fixation can be assessed.

By detecting the radial symmetry of foveal architecture, RBS directly assesses true foveal fixation of the eye and does not require eye-gaze calibration such as other methods of eye fixation detection. This advantage makes it possible to investigate less cooperative subjects, including young children at risk for developing amblyopia ("lazy eye"), which is the leading medical cause of decreased vision in childhood. Binocular RBS has the potential to screen young children for strabismus (misalignment of the eyes), the most common cause of amblyopia. Currently available vision screening devices can detect strabismus only indirectly via asymmetry of the positions of the corneal light reflexes.

RBS has demonstrated reliable and non-invasive detection of foveal fixation, as well as detection of strabismus. However, as with all polarization-sensitive technology used for retinal scanning and other intraocular assessment, RBS is adversely affected by corneal birefringence, which contributes most to the overall ocular birefringence and varies widely in both its amount (corneal retardance) and orientation (corneal azimuth) from one eye to the next, and across an individual pupil, thus creating variability in the RBS signal levels from one eye to the next and occasionally masking the desired signal from retinal birefringence.

Opto-mechanical designs that use wave plates ("waveplate-enhanced RBS") and other optical components that manipulate the polarization of light can be used to enhance foveal fixation detection while minimizing the deleterious effects of corneal birefringence in retinal birefringence scanning. In such a system, a double-pass half wave plate (HWP) spinning at a specific fractional frequency of the scanning frequency (f), more precisely at an odd multiple of $\frac{1}{16}$th as fast as the scanning frequency [($\frac{9}{16}$)f] is used, generating so-called "multiple-of-half" frequency components from birefringent patterns on the retina. For example, in one arrangement incorporating a double-pass fixed conventional wave plate in addition, 2.5f and 6.5f frequencies are generated with central fixation, and 3.5f and 5.5f frequencies are generated with off-center fixation. In addition, a high-amplitude 4.5f "spinning artifact" frequency is generated from interaction between the spinning half wave plate, the fixed conventional wave plate, and the corneal birefringence. A schematic design of this arrangement is illustrated in FIG. 1.

In the past, the azimuth and retardance of the double-pass fixed conventional wave plate were optimized for a large set of eyes with corneal birefringences representative across the population, considering only one of the predominant frequency components indicating central fixation (2.5f in that case), by calculating the minimal normalized standard deviation (standard deviated divided by the mean) of RBS signal strengths (FFT power) at that frequency (2.5f), and the wave plate with the minimal normalized standard deviation of RBS signal strengths at 2.5f was chosen to identify the best retardance/azimuth combination for the fixed wave plate to be added to the RBS system.

However, optimizing the fixed wave plate considering only one of the predominant frequency components results in a spinning artifact (4.5f signal in this particular optomechanical configuration) that is by no means uniform over the population range of corneal birefringence (see FIG. 2). While such optimization may generate results described as independent of fixation, independent of the state of eye fixation, independent of the fixation condition of the eye, the results are not independent of corneal birefringence! All eyes yield a very high to extremely high signal level for the spinning artifact frequency, but this level can vary significantly with the azimuth and retardance of the corneal birefringence of the eye that is measured. In other words, the spinning artifact is dependent on the corneal birefringence of an eye, that is, it is a function of corneal birefringence. A varying spinning artifact level can thus not properly be used for normalization of the RBS signal strengths. Also, if a varying signal level of the spinning artifact frequency is used to assess the focus of the eye during RBS testing, the signal-to-noise ratio of the focus signal would vary with the given eye's corneal birefringence, distorting the signal quality from one eye to the next. Thus to be used for these important purposes (normalization and "independent" focus assessment), the signal level of the spinning artifact frequency should be relatively independent of both the fixation condition and the corneal birefringence of the eye.

It would therefore be advantageous to provide a retinal birefringence scanner that is capable of providing a spinning artifact frequency signal level that is relatively independent of both the fixation condition and the corneal birefringence of an eye, in order to determine the goodness of eye fixation and eye focus.

SUMMARY OF THE INVENTION

In accordance with an embodiment, the present invention provides an apparatus and method for detecting fixation in at least one eye of a subject on a target comprising: a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein the optical illumination system further comprises a polarization modulating assembly configured to modulate the polarization of said illuminating beam; b) an optical detection system capable of detecting at least a portion of the illuminating beam of light of a) after being reflected back from the retina to provide a detection signal; c) a signal processing system adapted to communicate with the optical detection system to receive the detection signal; d) a signal analysis system adapted to communicate with the signal processing system to analyze the detection signal; wherein said polarization modulating assembly includes a thin-film-deposition optical element disposed at an oblique angle of incidence to said illuminating beam of light, said thin-film-deposition optical element serving as a wave plate having fixed retardance capable of being varied to optimize said detection signal; wherein the detection signal of b) has a first frequency signature when said subject's eye is fixed on said target, and a second frequency signature when said subject's eye is not fixed on said target; and wherein a combination of said first and second frequency signatures is used to assess the fixation state of said subject's eye.

In accordance with another embodiment, the present invention provides an apparatus and method for detecting fixation in at least one eye of a subject on a target comprising: a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein the optical illumination system further comprises a polarization modulating assembly configured to modulate the polarization of said illuminating beam; b) an optical detection system capable of detecting at least a portion of the illuminating beam of light of a) after being reflected back from the retina to provide a detection signal; c) a signal processing system adapted to communicate with the optical detection system to receive the detection signal; d) a signal analysis system adapted to communicate with the signal processing system to analyze the detection signal; wherein the detection signal of b) provides a first frequency signature when the subject's eye is fixed on said target, and provides a second frequency signature when the subject's eye is not fixed on said target, and a third frequency signature whenever the subject's eye is present and is reflecting light back into the detection system, and the third frequency signature is substantially independent of the fixation or non-fixation state of said subject's eye on said target; wherein a combination of first and second frequency signatures is used to assess the fixation state of said subject's eye; and wherein said third frequency signature is substantially independent of corneal birefringence of the subject's eye and is primarily a function of fundus reflectivity, refractive error, pupil size, and clarity of the ocular optical media, and is capable of being used to normalize the strengths of said frequency signatures assessing the fixation state of said subject's eye.

In accordance with a further embodiment, the present invention provides a method and apparatus for detecting the focus condition of at least one eye of a subject on a target, comprising: a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein the optical illumination system further comprises a polarization modulating assembly configured to modulate the polarization of said illuminating beam; b) an optical detection system capable of detecting at least a portion of the illuminating beam of light of a) after being reflected back from the retina to provide a detection signal; c) a signal processing system adapted to communicate with the optical detection system to receive the detection signal; d) a signal analysis system adapted to communicate with the signal processing system to analyze the detection signal; wherein the detection signal of b) provides a first frequency signature when the subject's eye is fixed on said target, and provides a second frequency signature when the subject's eye is not fixed on said target, and a third frequency signature whenever the subject's eye is present and is reflecting light back into the detection system, and the third frequency signature is substantially independent of the fixation or non-fixation state of said subject's eye on said target; and wherein said third frequency signature is substantially independent of the corneal birefringence of said subject's eye and is used to assess the goodness of focus of the eye.

In accordance with an aspect of the present invention, an apparatus for detecting fixation by an eye of a subject on a target includes a source of a polarized illuminating beam of light. The apparatus includes a polarizing beam splitter positioned such that a linearly polarized beam of light emitted from the source of the polarized illuminating beam of light is reflected by the polarizing beam splitter along an optical axis in a direction of the eye of the subject. The apparatus includes a scanner configured to create a circular scan on a retina of the eye of the subject with the polarized beam of light, wherein the polarized beam of light traverses retinal birefringent structures twice as it is reflected back toward the scanner, such that the scanner reflects the return beam of light back to the polarizing beam splitter. Additionally, the apparatus includes a photodetector. The return light is separated by the polarizing beam splitter into two orthogonally polarized components, such that a first polarized component is transmitted to the photodetector, and a second polarized component is reflected back to the source of the polarized illuminating beam of light. The apparatus also includes a half wave plate configured to rotate at a predetermined frequency, and being disposed between the polarizing beam splitter and the scanner and a non-rotating retarder tilted at an oblique angle to said optical axis and disposed between the half wave plate and the eye. The retardance of said non-rotating retarder is chosen, in combination with the speed of rotation of the half wave plate, to manipulate and modulate the polarization of the beams of light double-passing through them such that the polarization changes induced by said retinal birefringent structures are detected optimally by said photodetector.

In accordance with another aspect of the present invention, the non-rotating retarder includes a beam splitter/retarder achieving its retardance via tilting of its deposited thin-film coatings. The beam splitter/retarder includes a dichroic beam splitter having the additional function of reflecting a visible light target onto said optical axis for intended fixation by said eye. The non-rotating retarder is tilted at an oblique angle of an amount included within the range from 15 to 75 degrees from perpendicular to said optical axis; thereby efficiently reflecting non-wanted back reflections of the beam of light away from the apparatus to avoid contamination of the signal detected by the photodetector.

In accordance with yet another aspect of the present invention, a method for detecting fixation in an eye of a subject on a target including scanning at least a portion of a retina of an eye of a subject with an illuminating beam of light. The illuminating beam of light is polarized such that reflected portions of the illuminating beam are affected by birefringence of substructures of the retina. The method includes modulating the polarization of said illuminating beam and detecting at least a portion of the illuminating beam of light after being reflected back from the retina to provide a detection signal. Additionally, the method includes detecting a first frequency signature when the subject's eye is fixed on said target, detecting a second frequency signature when the subject's eye is not fixed on said target, and detecting a third frequency signature whenever the subject's eye is present and is reflecting light back into the detection system, wherein the third frequency signature is substantially independent of the fixation or non-fixation state of said subject's eye on said target, and wherein the third frequency signature is substantially independent of corneal birefringence via choice of the type of manipulation and modulation of the polarization of said illuminating beam. The method also includes using a combination of first and second frequency signatures to assess the fixation state of said subject's eye and using the third frequency signature, wherein said third frequency signature is primarily a function of fundus reflectivity, refractive error, pupil size, and clarity of the ocular optical media, to normalize the strengths of said frequency signatures assessing the fixation state of said subject's eye.

In accordance with still another aspect of the present invention, a method for detecting focus condition of at least one eye of a subject on a target includes scanning at least a portion of a retina of an eye of a subject with an illuminating beam of light, wherein the illuminating beam of light is polarized such that reflected portions of the illuminating beam are affected by birefringence of substructures of the retina and modulating the polarization of said illuminating beam. The method also includes detecting at least a portion of the illuminating beam of light after being reflected back from the retina to provide a detection signal and detecting a first frequency signature when the subject's eye is fixed on said target. The method includes detecting a second frequency signature when the subject's eye is not fixed on said target and detecting a third frequency signature whenever the subject's eye is present and is reflecting light back into the detection system. The third frequency signature is substantially independent of the fixation or non-fixation state of said subject's eye on said target, and the third frequency signature is substantially independent of corneal birefringence via choice of the type of modulation of the polarization of said illuminating beam. The method also includes using the third frequency signature to assess the goodness of focus of the eye.

In accordance with yet another aspect of the present invention an apparatus for detecting fixation by an eye of a subject on a target includes a source of a polarized illuminating beam of light and a non-polarizing beam splitter positioned such that a linearly polarized beam of light emitted from the source of the polarized illuminating beam of light is reflected by the non-polarizing beam splitter along an optical axis in a direction of the eye of the subject. The apparatus includes a scanner configured to create a circular scan on a retina of the eye of the subject with the polarized beam of light. The polarized beam of light traverses retinal birefringent structures twice as it is reflected back toward the scanner, such that the scanner reflects the return beam of light back to the polarizing beam splitter. The apparatus includes a dual-photodetector differential polarization detector. The return light is transmitted to the dual-photodetector differential polarization detector. Additionally, the apparatus includes a half wave plate configured to rotate at a predetermined frequency, and being disposed between the polarizing beam splitter and the scanner and a non-rotating retarder tilted at an oblique angle to said optical axis and disposed between the half wave plate and the eye. The retardance of said non-rotating retarder is chosen, in combination with the speed of rotation of the half wave plate, to manipulate and modulate the polarization of the beams of light double-passing through them such that the polarization changes induced by said retinal birefringent structures are detected optimally by said photodetector.

In accordance with another aspect of the present invention, the non-rotating retarder includes a beam splitter/retarder achieving its retardance via tilting of its deposited thin-film coatings. The beam splitter/retarder includes a dichroic beam splitter having the additional function of reflecting a visible light target onto said optical axis for intended fixation by said eye. The non-rotating retarder is tilted at an oblique angle of an amount included within the range from 15 to 75 degrees from perpendicular to said optical axis; thereby efficiently reflecting non-wanted back reflections of the beam of light away from the apparatus to avoid contamination of the signal detected by the photodetector.

DETAILED DESCRIPTION OF THE INVENTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In accordance with one or more embodiments, the present invention provides an apparatus for retinal birefringence scanning with a thin-film, dichroic beam splitter/retarder. Thin-film optics typically do not exhibit retardance at perpendicular incidence but do exhibit a type of "form" birefringence at oblique incidence (for example between 15 and 75 degrees incidence). For a particular example, at 45 degrees incidence, a dichroic beam splitter can be designed with the appropriate amount of transmission retardance to supply the fixed retardance function of a fixed wave plate as well as efficiently transmit the near-infrared scanning light from a laser diode and also efficiently reflect the visible light from a fixation target. A major advantage of using the 45° dichroic beam splitter to supply the necessary fixed retardance is that unwanted reflections from the surfaces of the beam splitter exit the optical system perpendicular to the optical axis and can easily be absorbed by a light trap, thereby no longer contributing to annoying stray light noise within the instrument. While an angle of 45° is shown in FIG. 3, the dichroic beam splitter can be positioned at any angle, typically between 15 and 75 degrees, that will provide the necessary fixed retardance, as well as efficiently transmit the near-infrared scanning light from the laser diode and also efficiently reflect the visible light from the fixation target.

Figure 3:
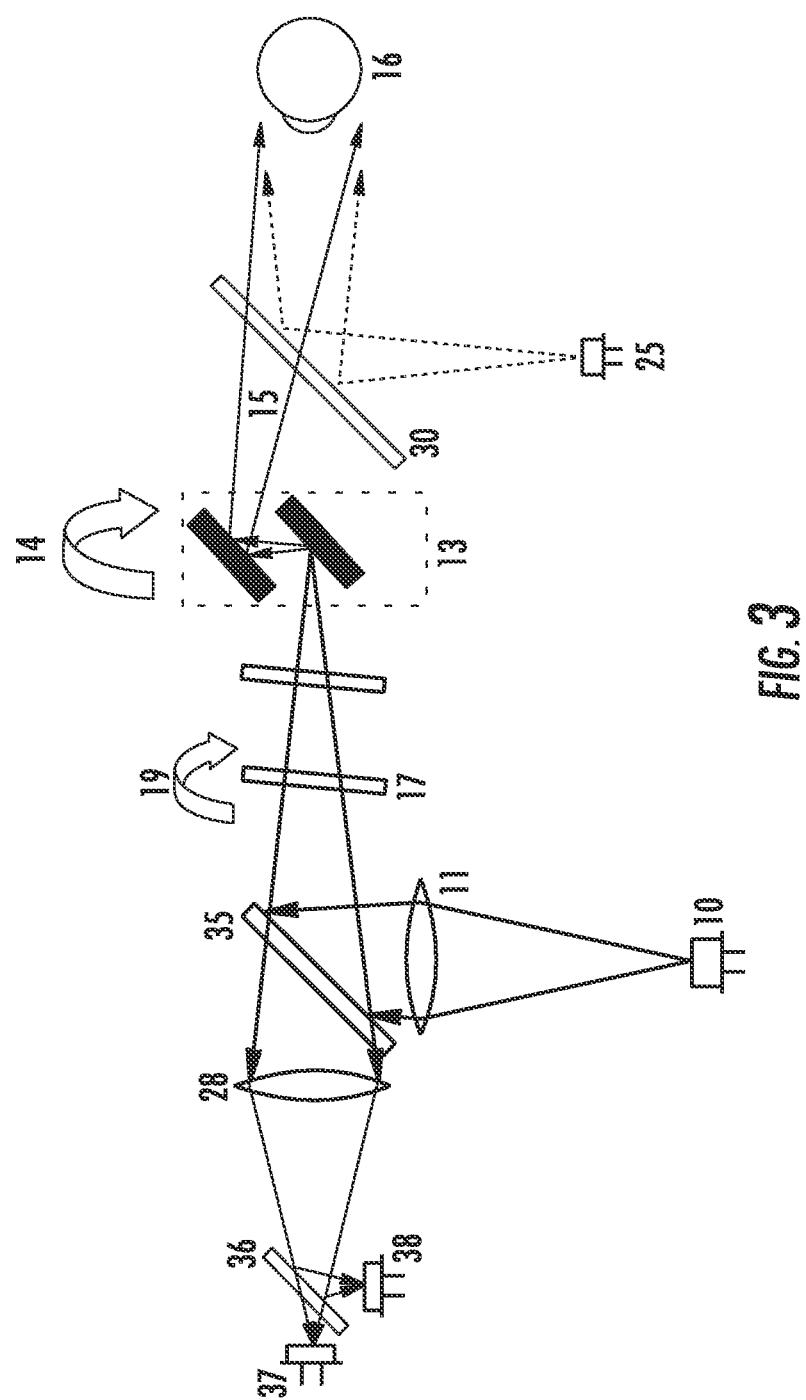
FIG. 3 illustrates a schematic diagram of an apparatus for retinal birefringence scanning including a 45°, thin-film, dichroic beam splitter/retarder, according to an embodiment of the present invention.

FIG. 3 illustrates an apparatus for retinal birefringence scanning including plane polarized near infrared light from a laser diode 10. Plane-polarized near-infrared light from laser diode 10 is converged by lens 11 and reflected by a non-polarizing beam splitter to come to a point focus within the 2-mirror scanning unit 13. Scanning unit 13 is rapidly rotated about the optical axis of the apparatus as indicated by arrow 14, at scanning frequency f, by conventional rotating means not shown. The scanned beam of light 15 diverges from scanning unit 13, pivoting about the center of the exit pupil of the apparatus which is substantially coincident with the entrance pupil of eye 16. Eye 16 sees a spinning circle of light with diameter subtending approximately 3° of visual angle. Between non-polarizing beam splitter 35 and scanning unit 13 is half wave plate 17. Half wave plate 17 is rotated about the optical axis of the apparatus as indicated by arrow 19, linked to the rotation of scanning unit 13, rotating at a different speed from the rotation speed of scanning unit 13, typically 9/16 times as fast as scanning unit 13 and rotating in the same direction. Half wave plate 17 is appropriately tilted to avoid interference from back reflections and rotates the plane of linear polarization of the light from laser diode 10 twice as fast as the speed of rotation of half wave plate 17, itself.

Diverging light from small visible light source 25 (typically a laser diode or light-emitting diode) is reflected toward eye 16 by dichroic beam splitter/retarder 30 to fill the exit pupil of the apparatus which is substantially coincident with the entrance pupil of eye 16. Eye 16 sees a fixed point of light in the center of the scanning circle formed by scanning unit 13, serving as the intended fixation point for eye 16. If eye 16 is focused on this fixation point from point source 25, then the scanning circle of light will also be imaged on the retina of eye 16.

The light entering eye 16 is changed in its polarization state by the corneal birefringence, which is relatively constant across the pupil, and is partially reflected from the fundus of eye 16, double-passing the retinal nerve fibers which exhibit "form" birefringence and further change the polarization state of the light depending upon the orientation and amount of retardance of the bundle of nerve fibers instantaneously traversed by the scanning spot of light. The polarization state of the reflected light from the fundus of eye 16 is changed again by the corneal birefringence as the light leaves the eye. The return path of the light from the eye is back through dichroic beam splitter/retarder 30, through scanning unit 13, and through spinning half wave plate 17.

With half-wave plate 17 spinning for example at 9/16ths of the spinning frequency (f) of scanning unit 13, proper fixation in the center of the scanning circle results in component frequencies of 2.5f and 6.5f. Off-center fixation results in component frequencies of 3.5f and 5.5f. The "spinning artifact" frequency is at 4.5f. These frequency components were predicted by mathematical modeling and have been confirmed experimentally.

The net effect of the half wave plate spinning at a particular fractional frequency of the scanning frequency f is the generation of frequency components for the central fixation and off-center conditions, as well as for the "spinning artifact," that are multiples of half of the scanning frequency. By digitally shifting the resulting periodic signal by one scanning period and subtracting it from itself, the desired multiples-of-half frequency components double in amplitude, and the unwanted frequency components that are whole multiples of the scanning frequency subtract out, significantly reducing optical noise from within the instrument ("360°-phase-shift subtraction"). Also, if the scanning frequency is chosen to be a harmonic of 60 Hz, for example 30 Hz or 60 Hz, periodic electromagnetically induced noise at 60 Hz will be subtracted out as well, a major advantage.

The two-mirror scanning unit 13 is one of many scanning unit designs that can be used. For example, a standard two-mirror galvanometer scanning unit can be used, or a spinning, slightly-tilted concave mirror can be used, the latter described for previous versions of retinal birefringence scanners for detection of eye fixation.

As noted, a fixed conventional wave plate can be problematic, in that it is difficult to find a tilt of this wave plate that prevents back-reflected light from introducing crippling stray light noise into the optical system. With the eye being tested typically returning less than 1/1000 of the light entering it, stray light in the optical system reaching the photodetector can severely degrade the obtained signals. In the present invention, this difficulty is eliminated by using a single thin-film, dichroic beam splitter/retarder placed at an oblique angle of incidence, typically at 45° in the original position of the pellicle beam splitter. FIG. 3 therefore illustrates a resultant apparatus for retinal birefringence scanning including the 45°, thin-film, dichroic beam splitter/retarder 30.

As illustrated in FIG. 3, the apparatus includes a single thin-film, dichroic beam splitter/retarder 30 placed at an oblique angle of incidence, typically at 45°, between an eye of the patient and two-mirror scanning unit 13. Reflections from the surface of dichroic beam splitter 30 exit the optical system perpendicular to the optical axis where they are absorbed by a conventional light trap, not shown. Such competing stray-light reflections must be assiduously suppressed from reaching the detector(s), because of the very low level of desired light reflected from the fundus of the eye. With the device illustrated in FIG. 3, there is at least a 27.5-fold reduction in stray light noise, with digital subtraction of background noise no longer being necessary.

Further illustrated in FIG. 3 is an arrangement for the illumination/detection system. The apparatus includes a 50:50 non-polarizing beam splitter 35, as illustrated in FIG. 3. Thus, at least half of the light from laser diode 10 is lost by transmission through non-polarizing beam splitter 35, and half of the light returning from the eye 16 is also lost by reflection from non-polarizing beam splitter 35 on the return path. However, as illustrated in FIG. 3, the apparatus can include polarizing beam splitter 36 and a pair of matched photodetectors 37 and 38. This arrangement of polarizing beam splitter 36 and photodetectors 37 and 38 in FIG. 3 constitutes a differential polarization detector, which can help minimize electronic noise by detecting the entire differential polarization signal, rather than by subsequent phase shift subtraction. However, the detected signals of interest in the apparatus of FIG. 3 will still be multiple-of-half frequency signals with respect to the scanning frequency f, and the phase shift method of doubling the desired signals and subtracting out the whole frequency signals can still be used. Alternately, a polarizing beam splitter can be used in place of the 50:50 non-polarizing beam splitter. In such an embodiment, a single photodetector can be used.

Figure 1:
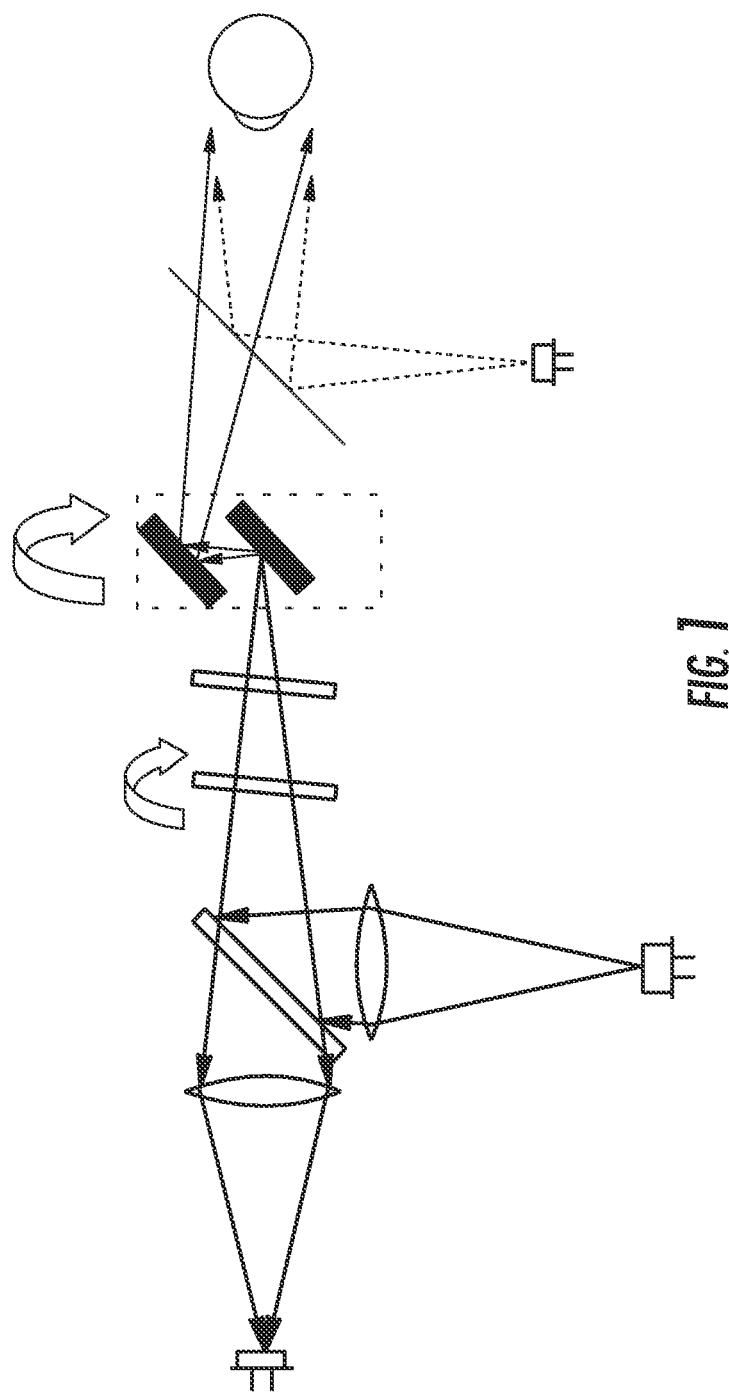
FIG. 1 illustrates a schematic diagram of prior-art waveplate-enhanced retinal birefringence scanning for the detection of eye fixation.
Figure 2:
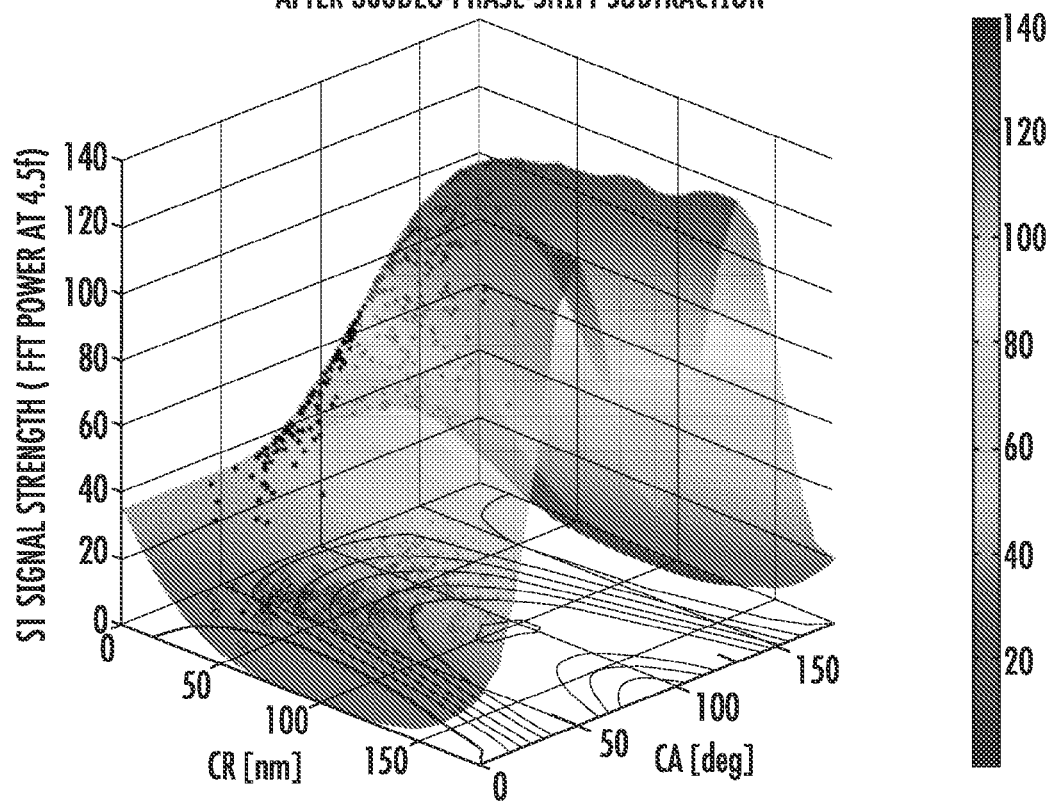
FIG. 2 illustrates a graphical view showing the signal strength of the spinning artifact frequency as a function of corneal retardance (CR) and corneal azimuth (CA). Representative eyes with known corneal birefringences are shown on the surface of the 3D-plot as black dots.

The present invention also provides methods for the optimization of the parameters of the spinning half wave plate and of a fixed conventional wave plate/retarder or dichroic beam splitter/retarder in the retinal birefringence scanning (RBS) design to enable important uses of the "spinning artifact" frequency component. These methods of optimization can apply to the inventive apparatus of FIG. 3, employing the dichroic beam splitter/retarder, and also to a fixed conventional wave plate, as illustrated in the apparatus of FIG. 1. The frequency of the "spinning artifact" component is determined by the half wave plate rotation speed and direction, and the amplitude is determined by interaction of the spinning half wave plate with any retardance encountered in the double-pass optics such as the fixed wave plate, the corneal birefringence, and the small amount of retinal birefringence. However, with optimum selection of the fractional spinning frequency of the half wave plate, and of the orientation and amount of retardance of the fixed wave plate, the "spinning artifact" frequency component can be made to be essentially independent of the fixation direction and also essentially independent of the range of corneal birefringence that exists across the population.

The fractional spinning frequency of half wave plate 17 in either apparatus of FIG. 1 or FIG. 3 can be chosen from a variety of fractional frequencies, most of which are an odd number of sixteenths of the scanning frequency f, which result in the desired signals being multiple-of-half frequencies of scanning frequency f Particularly large signals are obtained with a fractional spinning frequency of 9/16ths of the scanning frequency f, but other such fractional spinning frequencies will give good results as well.

The optimization methods of the present invention include calculating the normalized standard deviation (the standard deviation divided by the mean [or median]) of the sum of the RBS signal strengths at both central fixation frequencies (2.5f and 6.5f), and the normalized standard deviation of the RBS signal strength at the "spinning artifact" frequency (4.5f), for each retardance/azimuth combination in a database of 322 eyes. The minimum product of these normalized standard deviations is chosen to identify the best retardance/azimuth combination for the wave plate to be added (preferred embodiment):

$$\text{Min}\left[\frac{SD}{\text{mean}}[FFT_{2.5f} + FFT_{6\ldots 5f}] \cdot \frac{SD}{\text{mean}}[FFT_{4.5f}]\right]$$

Figure 4:
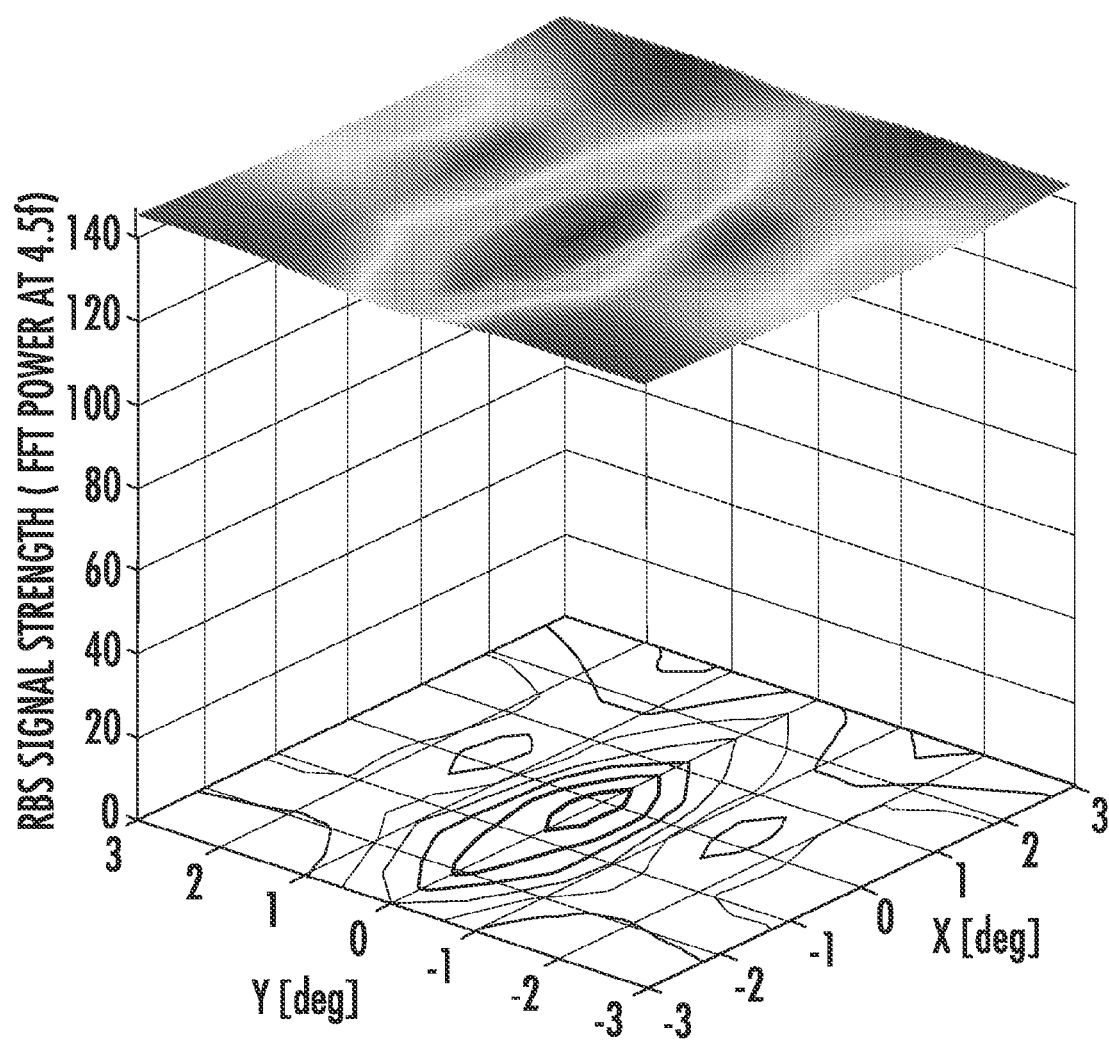
FIG. 4 illustrates a graphical view of signal strength of the "spinning artifact" frequency component (in a preferred embodiment) for an average right eye (CR=39 nm, CA=70°) in relative power units as a function of the horizontal and vertical distance from the foveal center, with the distance being expressed in degrees of visual angle.
Figure 5:
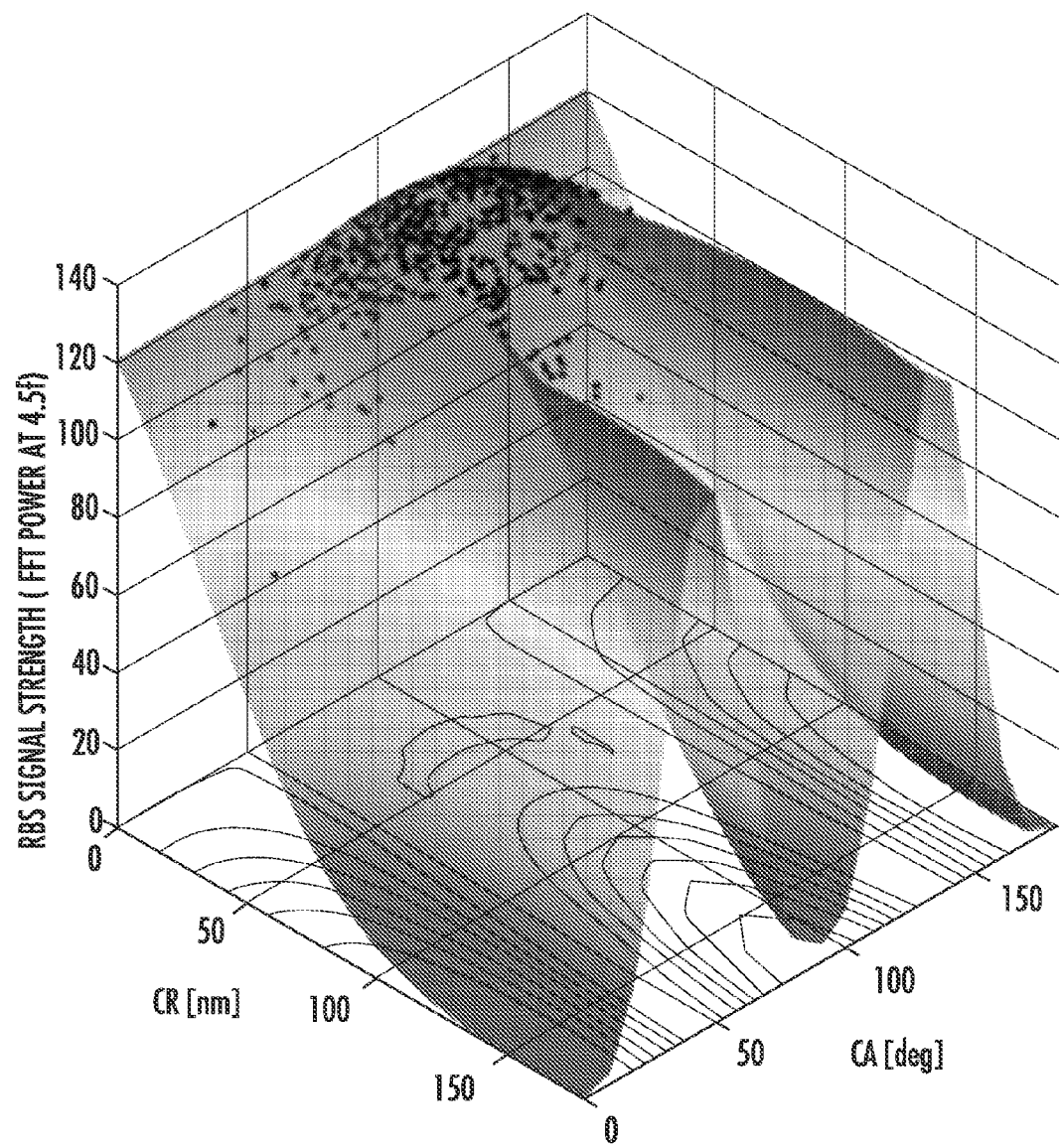
FIG. 5 illustrates a graphical view of signal strength of the "spinning artifact" frequency component (in the preferred embodiment) as a function of corneal retardance (CR) and corneal azimuth (CA). Representative eyes with known corneal birefringences are shown on the surface of the 3D-plot as black dots.
Figure 6:
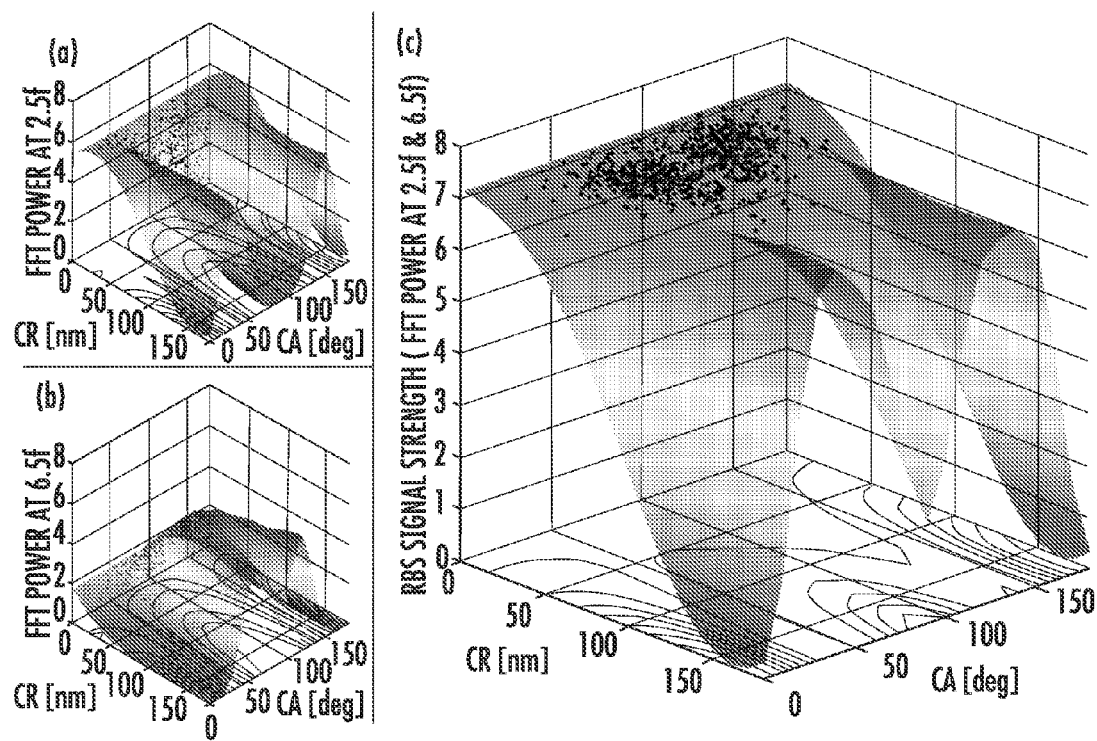
FIGS. 6A-6C illustrate graphical views of signal strength of central fixation frequencies (in preferred embodiment) (a=$FFT_{2.5f}$, b=$FFT_{6.5f}$, c=$FFT_{2.5f}$+$FFT_{6.5f}$) as a function of corneal retardance (CR) and corneal azimuth (CA). Representative eyes with known corneal birefringences are shown on the surface of the 3D-plots as black dots.

By considering these frequency components generated by the spinning HWP in the optimization process, the optimal fixed retarder can be chosen such that the "spinning artifact" frequency component at 4.5f becomes a function primarily of fundus reflectivity, refractive error, pupil size, and clarity of the ocular optical media, and is relatively independent of both the fixation direction (FIG. 4) and the corneal birefringence (FIG. 5) of the eye, fulfilling the requirement for normalization purposes and for robust focus detection. As can be seen in FIG. 6C, high and uniform differential RBS signals are obtained over more than the entire known range of corneal birefringence for both eyes, with both central fixation frequencies (2.5f and 6.5f) being considered in the analysis, as well as extremely high and relatively uniform signals at 4.5f (see FIG. 5). In this example, optimization was achieved with the fixed wave plate having a retardance of 74° and fast axis at 90° (essentially equivalent results were achieved with 106° retardance and 0° fast axis), which is a compromise between minimal normalized standard deviation of RBS signal strengths at 2.5f and 6.5f occurring with a retardance of 72° and fast axis at 90°, and that at 4.5f occurring with a retardance of 76° and fast axis at 90°.

Alternatively, the fixed wave plate is optimized by calculating the normalized maximum variation of RBS signal strength at the central fixation frequencies and "spinning artifact" frequency, for each retardance/azimuth combination, and the minimum product of normalized maximum variation is chosen to identify the best retardance/azimuth combination for the wave plate to be added:

$$\text{Min}\left[\frac{\max - \min}{\text{mean}}[FFT_{2.5f} + FFT_{6.5f}] \cdot \frac{\max - \min}{\text{mean}}[FFT_{4.5f}]\right].$$

Alternatively, the fixed wave plate may be optimized by choosing the wave plate with maximum product of mean [or median] signal strengths:

Max[mean[$FFT_{2.5f}$+$FFT_{6.5f}$]·mean[$FFT_{4.5f}$]].

Alternatively, the fixed wave plate may be optimized by choosing the wave plate with the minimum product of standard deviations, or with the minimum product of maximal variations:

Min[SD[$FFT_{2.5f}$+$FFT_{6.5f}$]·SD[$FFT_{4.5f}$]], or Min[max−min[$FFT_{2.5f}$+$FFT_{6.5f}$]·max−min[$FFT_{4.5f}$]].

Alternatively, the fixed wave plate may be optimized in the above ways but by choosing only the central fixation frequencies:

$$\text{Min}\left[\frac{SD}{\text{mean}}[FFT_{2.5f} + FFT_{6.5f}]\right],$$

$$\text{Min}\left[\frac{\max - \min}{\text{mean}}[FFT_{2.5f} + FFT_{6.5f}]\right],$$

Max[mean[$FFT_{2.5f} + FFT_{6.5f}$]],

Min[$SD[FFT_{2.5f} + FFT_{6.5f}]$],

Min[max − min[$FFT_{2.5f} + FFT_{6.5f}$]].

Alternatively the fixed wave plate may optimized in the above ways but by choosing only the spinning artifact frequency:

$$\text{Min}\left[\frac{SD}{\text{mean}}[FFT_{4.5f}]\right],$$

$$\text{Min}\left[\frac{\max - \min}{\text{mean}}[FFT_{4.5f}]\right],$$

Max[mean[$FFT_{4.5f}$]],

Min[$SD[FFT_{4.5f}]$],

Min[max − min[$FFT_{4.5f}$]].

The optimization methods described illustrate the value of the central fixation frequencies and the spinning artifact frequency in performing testing on a subject in order to detect fixation in an eye of the subject. For instance, as described above, fixation on the target at the center of the scanning circle produces signal components at 2.5f and at 6.5f. A high and uniform signal at 4.5f (the spinning artifact frequency) is also detected whenever an eye is present and reflecting light back into the detection system. When the scanned circle of light is decentered from the fovea, signals at 3.5f and 5.5f are detected. Thus the detection signal of the light reflected back from the retina provides a first frequency signature, such as the 2.5f and the 6.5f frequencies, when the subject's eye is fixed on said target. The detection signal provides a second frequency signature when the subject's eye is decentered from the target, such as the 3.5f and 5.5f frequencies. A third frequency signature (the spinning artifact frequency) is provided whenever the subject's eye is present and is reflecting light back into the detection system. The third frequency signature is substantially independent of the fixation or non-fixation state of said subject's eye on said target. A combination of the first and second frequency signatures is used to assess the fixation state of said subject's eye.

Additionally, the optimized third frequency signature is substantially independent of corneal birefringence of the subject's eye and primarily a function of fundus reflectivity, pupil size, and clarity of the ocular optical media, and is capable of being used to normalize the strengths of said frequency signatures assessing the fixation state of said subject's eye. Also, the third frequency signature can be used to measure the quality of the focus of the subject's eye.

The first frequency signature includes at least one frequency component that is directly proportional to said scanning frequency by a first proportionality constant. The second frequency signature includes at least one frequency component that is directly proportional to said scanning frequency by a second proportionality constant. Similarly, the third frequency signature includes at least one frequency component that is directly proportional to said scanning frequency by a third proportionality constant. The first proportionality constant has a different value from a value of the second proportionality constant and from a value of the third proportionality constant.

EXAMPLE

An exemplary implementation of the present invention is included hereinafter simply by way of example and in no means is meant to be considered limiting. Because of the strict radial symmetry of the Henle fibers about the eye's fovea, RBS causes the polarization state of the light to change at whole multiples of the frequency of the circular scan, for example, at twice or four times the scanning frequency. By incorporating and spinning a double-pass half wave plate (HWP) at a specific fractional frequency—more precisely, at an odd multiple of ¹⁄₁₆th of the scanning frequency (f)—the axis of polarization of the impinging light can be continuously rotated to modulate the polarization-related changes arising from the retina—the RBS signal—such that they occur at multiples-of-half of the scan frequency after double-passing through the birefringent radial array of Henle fibers.

In the exemplary embodiment, the continuous change of polarization orientation by spinning the HWP also enables determination of different polarization states with a single analyzer/photodetector per eye, at different points in time. This is because, on alternate 360° scans, the polarization state of the incident light striking a given patch of Henle fibers is rotated to a new azimuth. Use of a single photodetector (per eye) eases optical fabrication and alignment tolerances, as well as simplifies the electronics, as compared with conventional polarizing beam splitter/dual-photodetector RBS arrangements.

Thus with different polarization measurements being represented in the recorded RBS signal one scanning cycle apart, a differential polarization signal is obtained by shifting a copy of the recorded signal by one scanning period (360°), and subtracting it from the original signal ("360°-phase-shift subtraction"). This causes the desired signal components to double in amplitude, and even quadruple in signal strength (FFT power). The amplitude doubling occurs because on alternate 360° scans the signal components with a frequency of a multiple of half the scan frequency differ by a 180° phase shift, so that when the alternate 360° scans are subtracted from one another, the amplitudes of these "half-frequency" signal components double.

Light that has been depolarized by reflection from the skin and/or the sclera is not affected by the spinning HWP, such that this source of optical background noise repeats over a single scanning cycle and will occur at a whole multiple of the scanning frequency. Any such signal component with a frequency of a whole multiple of the scanning frequency will be eliminated by the 360°-phase-shift subtraction because each whole-number frequency signal will be in phase with itself when shifted by 360° and will thus be eliminated on subtraction.

In addition to the spinning double-pass HWP, a fixed double-pass wave plate is used to enable detection of the differential RBS signal essentially independently of the amount and orientation of corneal birefringence, which varies from person to person and from eye to eye. To achieve this goal, the characteristics of both wave plates were optimized using an algorithm implemented in a custom RBS computer program in MATLAB, which was based on Müller-Stokes-matrix calculations and corneal birefringence measurements from a dataset of 322 human eyes. This dataset was representative of the general population and included 150 adult eyes and 172 eyes from a recent study that included children. A detailed description of the optimization procedure is provided below.

An algorithm was developed and implemented in a computer model in MATLAB to find the HWP rotation speed (that is, the specific odd multiple of 1/16th of the scanning frequency, f) that statistically maximizes the RBS-signal strength (FFT power at particular half-multiples of the frequency) for the 322 eyes in the dataset. Corneal birefringence is highly correlated between right and left eyes and is approximately symmetric about 90° CA. Thus, to derive a method that is essentially independent of right- and left-eye corneal birefringences, the mirror image of each eye (mirrored about 90° CA) was included in the assessment to yield a total of 644 "eyes."

In the exemplary RBS computer model, which simulates RBS in a double-pass system, every component of the eye is characterized by its own Müller matrix, M, with the fundus treated as a complete polarization-preserving ideal reflector that is modeled by the Müller matrix of an ideal mirror. The cornea and the retina are considered to be birefringent media that affect the polarization state of light passing into and, upon fundus-reflection, back out of the eye (that is, a double-pass effect). More precisely, the cornea is modeled as a linear retarder with a specific corneal retardance CR and corneal azimuth CA where the latter represents the fast axis. The retina (in this case, the Henle fiber layer) is modeled as a radially birefringent medium with the maximum single-pass retardance located approximately 1.5° from the foveal center (the maximum retardance is considered to be 7° for consistency with previously used values, whereas this value is closer to 8-9° for an operating wavelength of 785 nm as used in the exemplary RBS system).

With the eye fixating properly on the central fixation point in the center of the 3° circular scan, the stack of Henle fibers at each point where the light strikes is about 1.5° from the foveal center. The Henle fiber layer therefore acts as a radially-disposed linear retarder with a retardance of approximately 7°. Thus during central fixation, the circular scan on the retina can be simulated as a spinning wave plate with a retardance $\delta_r = 7°$ and a fast-axis orientation $\theta_r$ rotating at f.

Similarly, the spinning HWP was modeled by the Müller matrix of a retarder with retardance $\delta_{HWP} = 180°$ and a fast-axis orientation $\theta_{HWP}$. The latter changes continuously with time at an odd multiple of 1/16th of the scanning frequency or angular rotation of the 7° wave plate:

$$\theta_{HWP} = (2n+1) \cdot \frac{\theta_r}{16} = (2n+1) \cdot \frac{\omega_r t}{16} = (2n+1) \cdot \frac{2\pi f t}{16}$$

During simulated central fixation, a beam of initially vertically polarized light (before passage through the cornea), described by the Stokes vector, $\vec{S}_{in} = (1,-1,0,0)^T$, was scanned on the retina. This beam continuously changed the orientation of its linear polarization after passing through the spinning HWP. The outgoing Stokes vector, $\vec{S}_{out}$, determines the final polarization state:

$$\vec{S}_{out} = M_{HWP(out)}(\delta_{HWP}, -\theta_{HWP}) \cdot M_{cornea(out)}(CR, -CA) \cdot \\ M_{retina(out)}(\delta_r, -\theta_r) \cdot M_{fundus} \cdot \ldots \cdot M_{retina(in)}(\delta_r, \theta_r) \cdot \\ M_{cornea(in)}(CR, CA) \cdot M_{HWP(in)}(\delta_{HWP}, \theta_{HWP}) \cdot \vec{S}_{in}$$

Optimization was achieved by varying n from 0 to 7. For each HWP rotation frequency ($f_{HWP} = 1/16, 3/16, 5/16, \ldots, 15/16$ times f), the relevant half-multiples of the frequency components in the RBS signal (Stokes parameter $S_1$) were determined. At each determined frequency component, the FFT power was computed for each of the representative CR and CA combinations in the dataset. The sum of the RBS-signal strengths for the 644 "eyes" was calculated for a given frequency, and the HWP rotation frequency with the highest number (maximum sum) was chosen as the best rotation speed.

Figure 7:
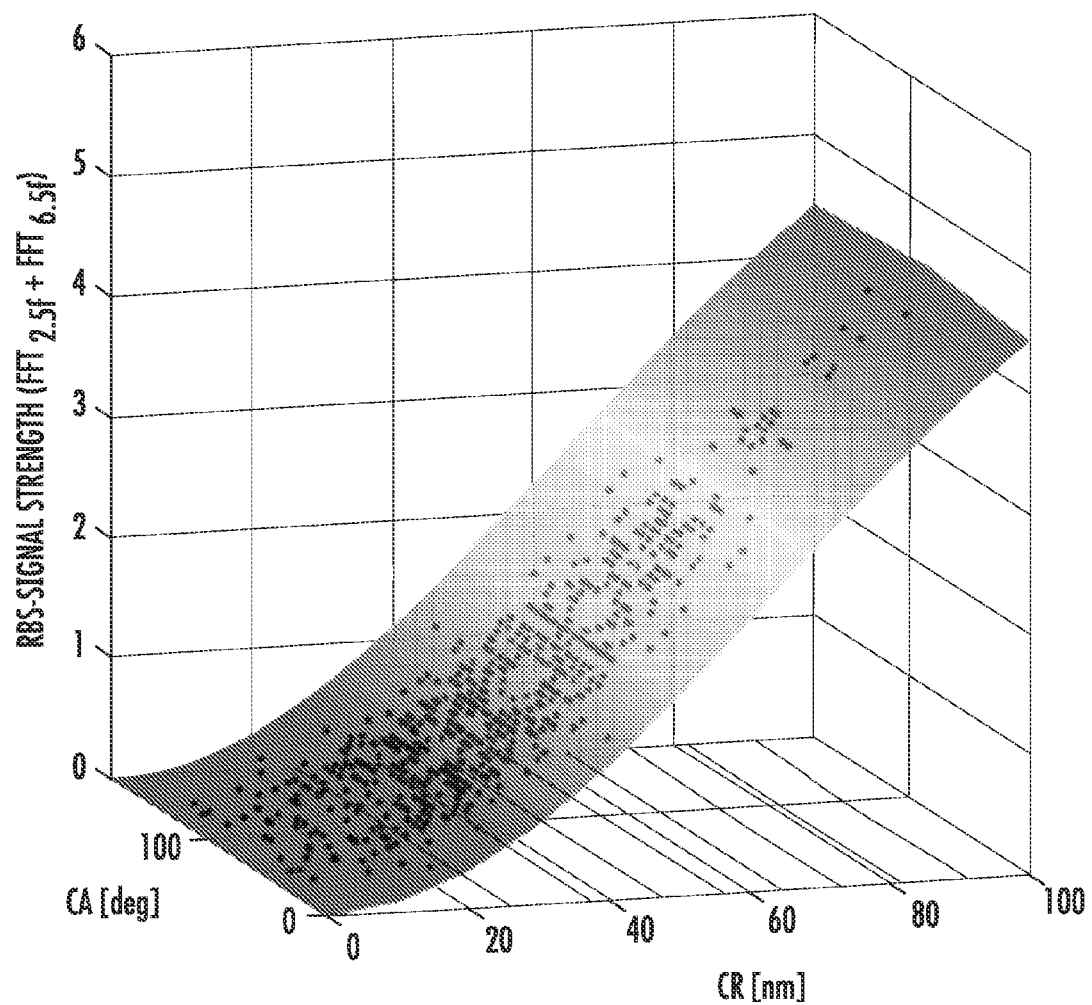
FIG. 7 illustrates a graphical view of simulated results using a single photo-detector RBS system with a HWP spinning at ($9/16$)f, according to an embodiment of the present invention. Differential RBS-signal strength at 2.5f (with a minor contribution at 6.5f for eyes with high corneal retardance) is shown in relative power units as a function of CR and CA during simulated central fixation. For demonstration purposes, the RBS-signal strengths at the two center frequencies are added ($FFT_{2.5f}+FFT_{6.5f}$). The right and left eyes from the available dataset are shown as black dots on the surface of the 3D-plot.

Spinning the HWP at (9/16)f maximized the RBS-signal strength for the representative 644 "eyes." At this particular rotation speed, the modulation caused by the HWP causes the polarization-related changes arising from the Henle fibers to occur predominantly at 2.5f (with a minor contribution at 6.5f for eyes with high CR). However, the full advantage of the RBS approach using a spinning HWP cannot be appreciated when the subject's CR is low or close to zero. FIG. 7 shows a three-dimensional (3D) plot of differential RBS signal strength (FFT power) at 2.5f and 6.5f as a function of CR and CA, during simulated central fixation. Superimposed on the 3D plot are the signal strengths for the representative 644 "eyes." The 3D plot indicates that the RBS signal falls off with low values of CR and goes to zero when CR is zero. Thus an amount of artificial "corneal" birefringence has to be added to the design in the form of a double-pass wave plate to make the distribution of signal strengths more uniform across the potential combinations of CR and CA.

In order to select the optimal double-pass wave plate that will statistically maximize RBS-signal strength, in combination with the double-pass HWP spinning at (9/16)f while minimizing the variability across corneal birefringences, a wave plate (WP) with unknown retardance, $\delta_{WP}$, and fixed azimuth, $\theta_{WP}$, was inserted into the equation for $\vec{S}_{out}$ above:

$$\vec{S}_{out} = M_{HWP(out)}(\delta_{HWP}, -\theta_{HWP}) \cdot M_{WP(out)}(\delta_{WP}, -\theta_{WP}) \cdot$$
$$M_{cornea(out)}(CR, -CA) \cdot \ldots \cdot M_{retina(out)}(\delta_r, -\theta_r) \cdot$$
$$M_{fundus} \cdot M_{retina(in)}((\delta_r, \theta_r) \cdot M_{cornea(in)}(CR,$$
$$CA) \cdot \ldots \cdot M_{WP(in)}(\delta_{WP}, \theta_{WP}) \cdot M_{HWP(in)}(\delta_{HWP},$$
$$\theta_{HWP}) \cdot \vec{S}_{in}$$

The solution was optimized by computing the mean and standard deviation of the RBS signal strengths for the 644 "eyes" in the dataset for each retardance/azimuth combination of the wave plate. The standard deviation was then divided by the mean to result in the normalized standard deviation for this particular retardance/azimuth combination of the wave plate. The retardance/azimuth combination with the minimum normalized standard deviation was chosen to identify the best wave plate to be added.

The frequencies of the half-multiple frequency components within the RBS signal that indicate central fixation are determined by the interaction of the spinning HWP with the radial, birefringent Henle fiber layer. These frequencies are 2.5f and 6.5f when the HWP is spun at (9/16)f Another half-multiple frequency component (4.5f) occurs in the signal whose frequency is determined by the fractional frequency of the HWP alone. This 4.5f signal is thus inherently independent of the fixation condition of the eye and is referred to as the 'spinning artifact' frequency component. When the system is configured such that it is also relatively independent of corneal birefringence, the spinning artifact can be used to great advantage for normalization purposes. This normalization is necessary to compensate for variations in fundus reflectivity, refractive error, pupil sizes, light levels, and dust that accumulates on the optics over time.

The minimal normalized standard deviation of RBS-signal strengths was thus calculated at the central frequencies 2.5f and 6.5f and also at the spinning artifact frequency 4.5f for each retardance/azimuth combination of the wave plate. The minimum product of normalized standard deviations was chosen to identify the best retardance/azimuth combination for the fixed wave plate as follows:

$$\text{Min}\left[\frac{SD}{\text{mean}}[FFT_{2.5f} + FFT_{6.5f}] \cdot \frac{SD}{\text{mean}}[FFT_{4.5f}]\right]$$

With the scanning circle becoming decentered from the foveal center (paracentral fixation), the retina can no longer be considered a rotating wave plate with the same amount of retardance at each scanning position and an azimuth of foveal birefringence that rotates through 360°. Both foveal retardance and fast-axis orientation change depending on the momentary scanning position. $\delta_r$ specifically depends on the distance from the foveal center and increases from zero in the very center to a maximum at about 1.5° from the foveal center, as mentioned above. From that position, the retardance subsequently tapers off with increasing distance from the foveal center:

$$\delta_r = \left(\prod_{i=1}^{2} e^{-\frac{r}{\tau_i}}\right)\left(\prod_{i=3}^{5} \left(1 - e^{-\frac{r}{\tau_i}}\right)\right)$$

where $\tau_1 = 3.7$, $\tau_2 = 50$, $\tau_3 = 0.6$, $\tau_4 = 5$, and $\tau_5 = 0.8$. Because it is perpendicular to the fiber orientation, $\theta_r$ is calculated as follows during paracentral fixation $$\theta_r = \tan^{-1}\left(\frac{R\sin(\varphi) + y_{ret}}{R\cos(\varphi) + x_{ret}}\right) + 90°$$

where $\phi$ is the momentary scanning position, which advances through 360°, and $x_{ret}$ and $y_{ret}$ are the horizontal and vertical displacements of the center of the scanning circle from the foveal center, respectively.

Figure 8:
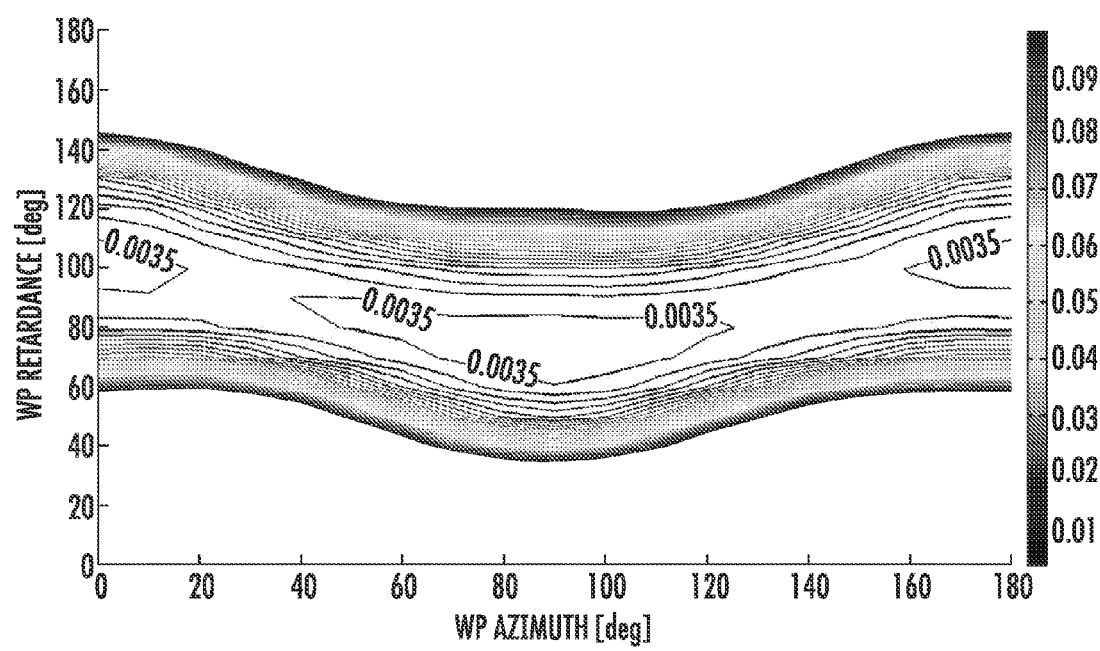
FIG. 8 illustrates a contour plot of the product of the normalized standard deviation of RBS signal strengths at the central fixation frequencies (2.5f and 6.5f) and the spinning artifact frequency (4.5f) for the 644 "eyes" in the dataset, shown as a function of retardance and azimuth (fast axis orientation) of the double-pass fixed wave plate, with contours plotted only below a level of 0.1.

Foveal fixation detection was optimized with the HWP spinning at (9/16)f and with the fixed wave plate having a retardance of 74° and a fast axis vertical at 90°. This fixed-wave plate configuration gives essentially equivalent results as a fixed wave plate with a 106° retardance and a 0° fast axis, which can be appreciated by FIG. 8; both a 74° wave plate (WP) with fast axis at 90° and a 106° wave plate with fast axis at 0° fall within the annotated "0.0035" contour where the product of normalized standard deviation is below 0.0035 and the results are reasonably comparable. At (9/16)f the modulation produced by the HWP causes the polarization-related changes that arise from the retina's Henle fibers during central fixation (that is, with the scanned circle of light centered on the fovea) to occur at 2.5f and 6.5f Another half-multiple frequency component (4.5f) occurs in the signal at a high amplitude, the frequency of which is determined solely by the HWP rotation speed. This "spinning artifact" frequency is thus inherently independent of the eye's fixation (FIG. 9F).

Figure 9:
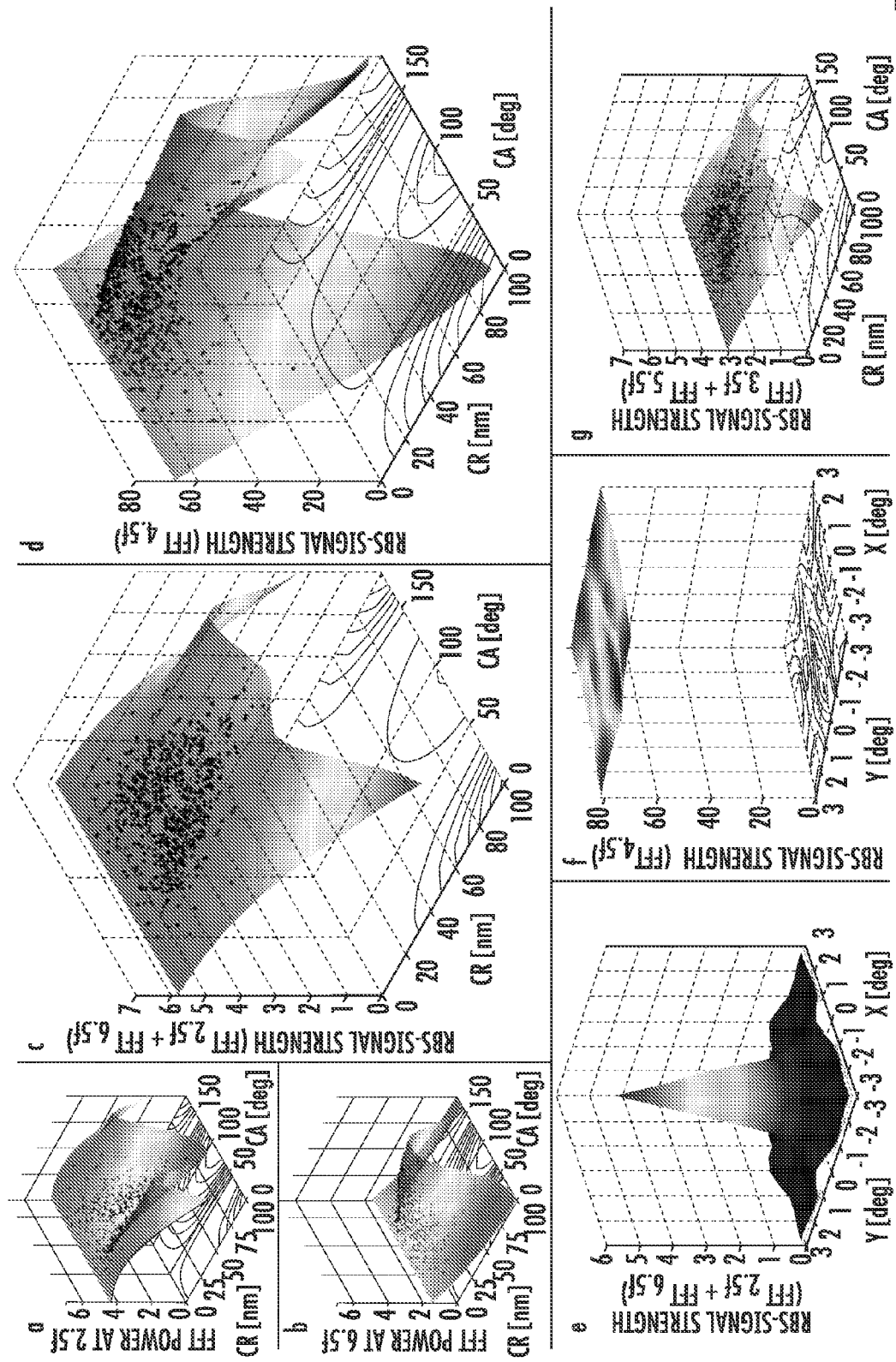
FIGS. 9A-9G illustrate a graphical view of simulated results using the polarization-modulated technique; with HWP spinning at $(9/16)f$ and fixed 74° wave plate at 90°, according to an embodiment of the present invention.

FIGS. 9A-9G show the simulated results obtained using the optimized design with the HWP spinning at (9/16)f and a fixed 74° wave plate at 90°. FIGS. 9A-9D show a three-dimensional (3D) plot of differential RBS signal strength (FFT power) at the frequencies of interest (2.5f, 6.5f 4.5f) as a function of CR and CA, during simulated central fixation. Superimposed on the 3D plot are the signal strengths for the representative eyes from the dataset. The data indicate that when both of the central fixation frequencies, 2.5f (FIG. 9A) and 6.5f (FIG. 9B), are considered in the analysis (FIG. 9C), strong and essentially uniform differential RBS signals are obtained over the entire known range of corneal birefringence for both eyes. Extremely high and relatively uniform signals are also obtained at a frequency of 4.5f (FIG. 9D).

A spatial representation of RBS-signal strengths at 2.5f and 6.5f for a typical right eye (CR=39 nm, CA=70°; statistical average of right eyes from the dataset) is depicted in FIG. 9E. As expected, a definite signal maximum can be seen at the foveal center (0,0) that falls off away from the center. The full-width of the distribution at half-maximum (FWHM) is approximately ±0.75°. In contrast, the spatial distribution of the RBS signal at 4.5f is essentially uniform with decentration (FIG. 9F). Because the amplitude of this spinning artifact frequency is independent of both corneal birefringence and fixation direction, it can be used to perform normalization across different ocular reflectivities, refractive errors, pupil sizes, and other parameters. These results show that eye fixation can be detected by computing the combined powers at 2.5f and 6.5f normalized by the power at 4.5f.

Fourier analysis of the RBS signal revealed that other frequencies (3.5f and 5.5f) appear during simulated paracentral fixation (that is, with the scanned circle of light decentered from the fovea) (FIG. 9G). These data indicate that although the overall RBS-signal strength at these paracentral frequencies is also essentially independent of corneal birefringence, it is somewhat lower than the RBS-signal strength at 2.5f and 6.5f during simulated central fixation (FIG. 9C).

Central fixation may thus be confirmed by strong signal strength at 2.5f and/or 6.5f and little or no signal strength at 3.5f and/or 5.5f Conversely, paracentral fixation may be detected, if desired, by moderate signal strength at 3.5f and/or 5.5f and little or no signal strength at 2.5f and/or 6.5f.

Figure 10:
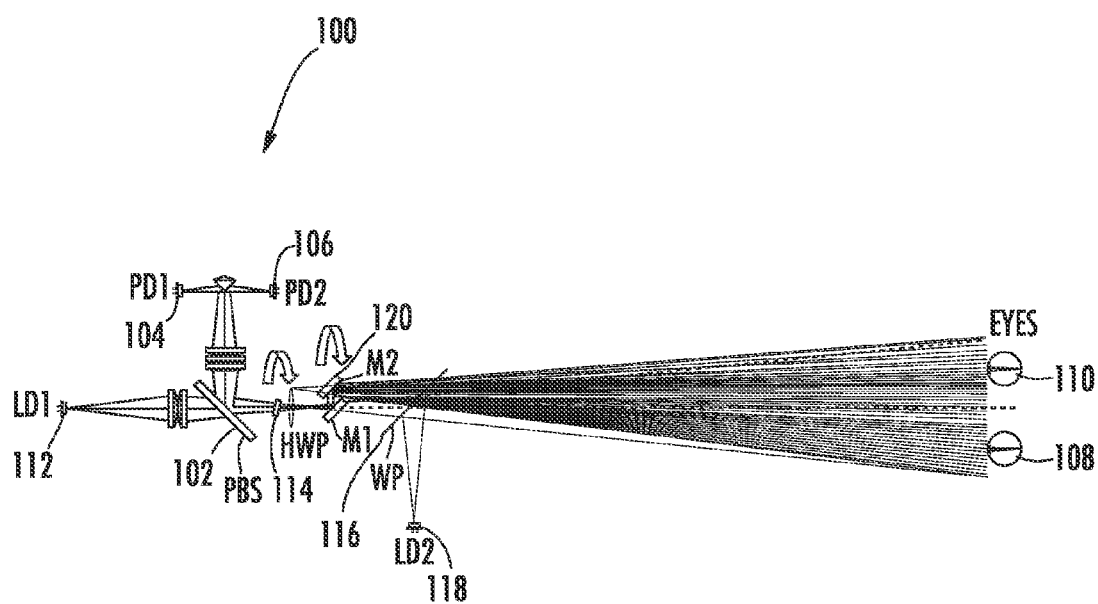
FIG. 10 illustrates a schematic diagram of an experimental validation set-up, implementing the polarization-modulated technique with the HWP spinning at $(9/16)f$ and fixed 106° wave plate at 0°, according to an embodiment of the present invention.

To enable validation of the eye-fixation detection method, we built a binocular eye-fixation monitor (FIG. 10), implementing the computer-model-optimized, polarization-modulated RBS technique (with the HWP spinning at $(9/16)f$ and a fixed dichroic mirror/wave plate with retardance of 106° and fast axis at 0°; f=30 Hz). The apparatus 100 as illustrated in FIG. 10 includes a polarizing beam splitter 102, with a single photodetector 104, 106 for each eye 108, 110. Light is generated by a source of polarized light 112. The two exit pupils at the subject's eye plane are large, each approximately 40 mm×40 mm, enabling testing of the subject using a hand-held instrument. Half wave plate 114 is configured to spin at $(9/16)f$ and a fixed dichroic mirror/wave plate 116 with retardance of 106° is positioned with fast axis at 0°; f=30 Hz. A second light source 118 is optically conjugate to light source 112, taking into account the longitudinal chromatic aberration of eyes 108 and 110, and is reflected toward the eye by the dichroic mirror/wave plate 116. The apparatus also includes a two-mirror scanning unit 120.

Two human subjects were studied, including a 29-year-old individual with emmetropic eyes (no refractive error) and a 67-year-old presbyopic individual with essentially no remaining focusing ability and with mild nuclear sclerotic cataracts in both eyes.

Figure 11A:
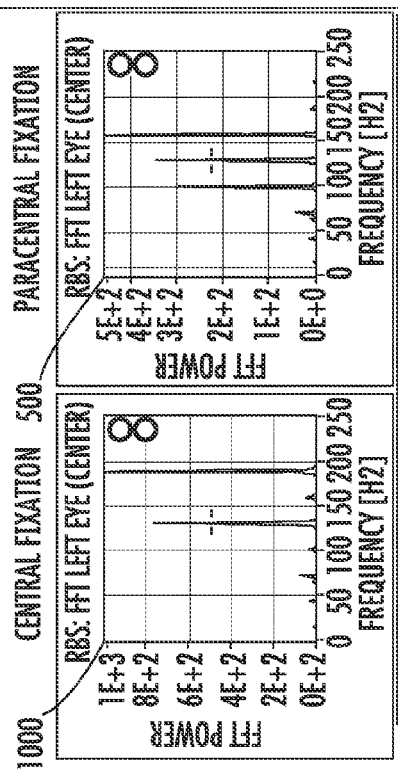
FIGS. 11A-11E illustrate graphical representations of experimental results from human eyes, according to an embodiment of the present invention.

Results obtained using the binocular eye-fixation monitor are depicted in FIGS. 11A-11E and FIG. 12. The data in FIG. 11A are shown as an FFT power spectrum of the differential polarization signals (after 360°-phase-shift subtraction) from the 29-year-old's emmetropic (no refractive error) left eye [CR=37 nm, CA=104°, measured separately with a GDx-VCC instrument (Carl Zeiss Meditec AG, Jena, Germany)] during central and paracentral fixation. As predicted, during central fixation (on a blinking target presented in the center of the scanned circle) and thus with the scanned circle of light centered on the fovea, the signal had a strong 195-Hz (6.5f) component, a strong 135-Hz (4.5f) component and a minor contribution at 75 Hz (2.5f). As expected, the signals at 195 Hz and 75 Hz essentially disappeared during paracentral fixation while the 135-Hz component remained. During paracentral fixation on the edge of the red scanning circle (1.5° away from the center), the signal had a predominant 165-Hz (5.5f) component and a 105-Hz (3.5f) component. In accordance with the modeling results, the combined power at these frequencies is lower than that of the 195-Hz (6.5f) and 75-Hz (2.5f) components observed during central fixation. These results confirm that the presence and absence, respectively, of the 2.5f and 6.5f frequency components indicate central and paracentral fixation, and that the 4.5f spinning artifact is suitable for normalization purposes. As a result, the combined powers at 2.5f and 6.5f normalized by the power at 4.5f $[(FFT_{2.5f}+FFT_{6.5f})/FFT_{4.5f}]$ can be used to assess foveal fixation of an eye.

Figure 11B:
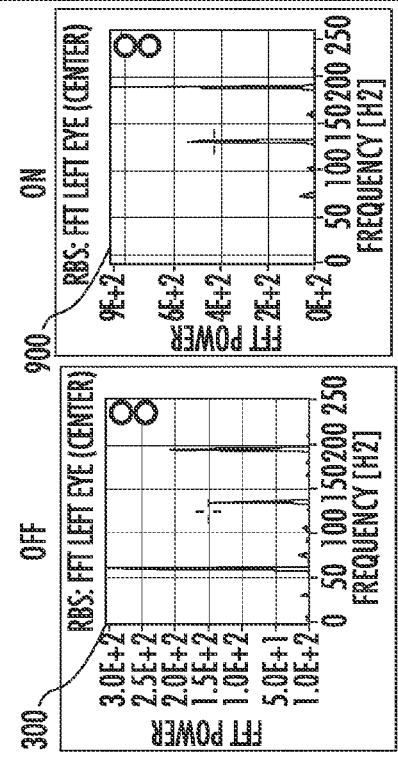

FIG. 11B shows the central fixation signal from the 29-year-old's emmetropic right eye (CR=34 nm, CA=77°) with and without 360°-phase-shift subtraction. As expected, noise at whole multiples of the scanning frequency (harmonics of the 30-Hz scanning frequency) is eliminated when 360°-phase-shift subtraction is performed (note the disappearance of the 60 Hz signal), and the signals of interest at half-multiples of the frequency (such as at 135 Hz and 195 Hz) are nearly quadrupled in strength. With eyes closed or with no subject in front of the system, very low noise levels at the frequencies of interest were measured (FIG. 11C), yielding a SNR in the order of 100 or more with the new technique. This confirms that—in contrast to previous RBS systems with SNRs as low as 0.11—preliminary eyes-closed background measurements to be subtracted later are not required for the polarization-modulated RBS method of the present invention.

Figure 11D:
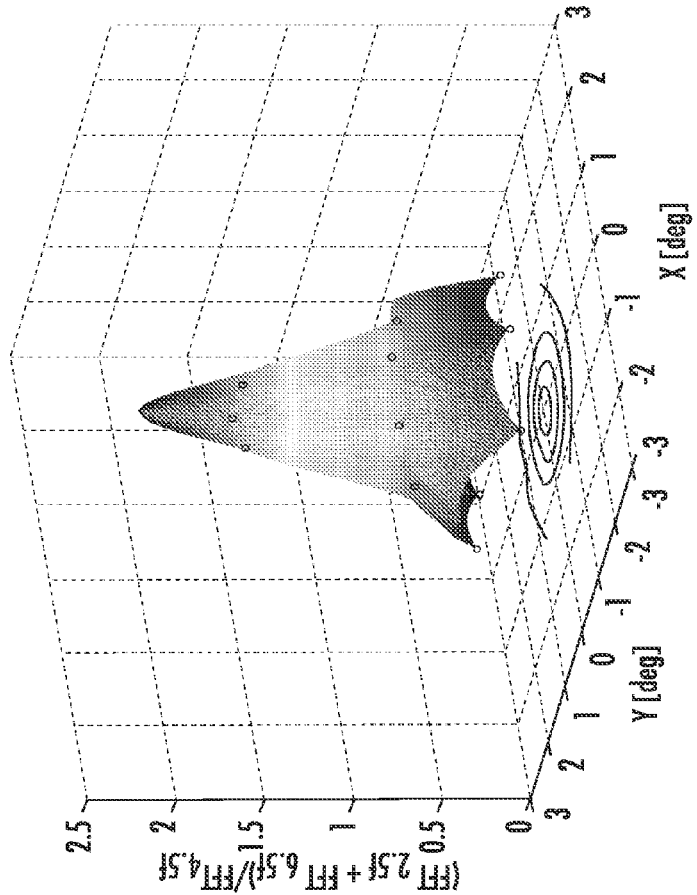
Figure 11E:
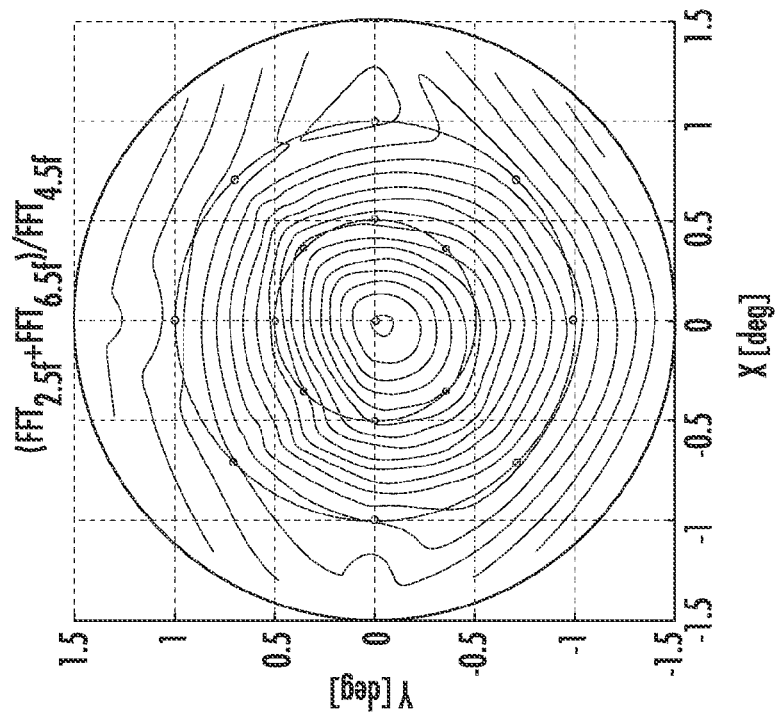
Figure 11C:
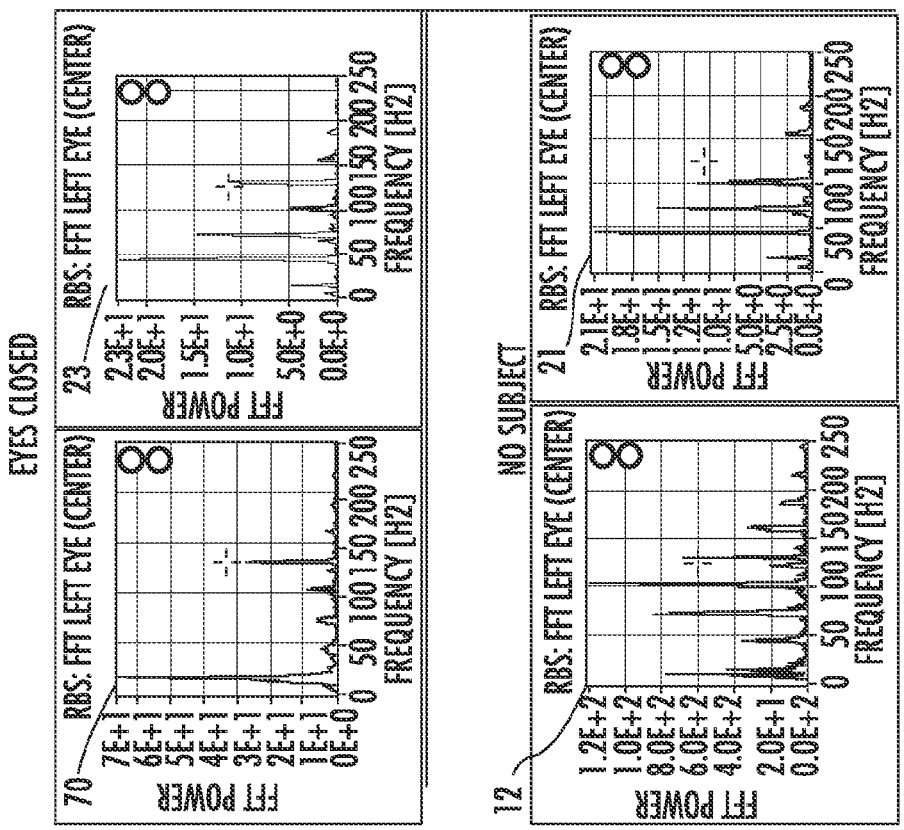

In order to assess accuracy and spatial resolution of the eye-fixation detection method, the subject was asked to fixate centrally on the blinking target and then to fixate paracentrally on various points on a projected grid that represented displacements from 0.5° to 1.5° away from the center in 0.5° increments along eight half-meridians (as indicated in FIG. 11E). The spatially-mapped distribution of the indicator of foveal fixation, $[(FFT_{2.5f}+FFT_{6.5f})/FFT_{4.5f}]$, obtained from the emmetropic right eye is shown in FIGS. 11D-11E. The curve's peak is located very close to (0°,0°) with an FWHM of approximately ±0.75°. This agrees with the predictions from the simulated results; FIG. 9E). The half-maximum was taken as the preliminary threshold setting to differentiate between central and non-central fixation even in eyes expected to generate low-level signals, such as eyes with high refractive errors or media opacities.

Figure 12:
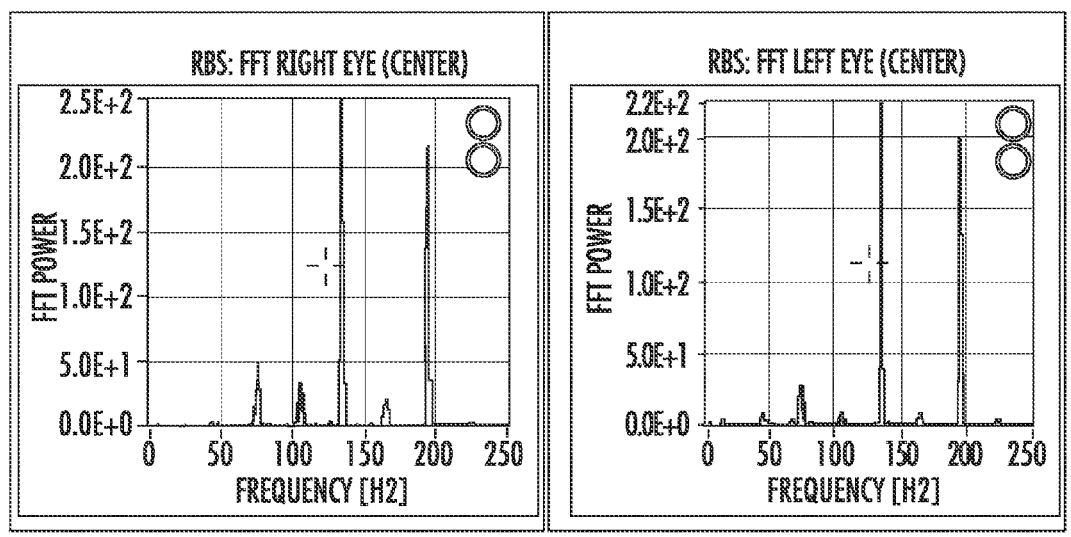
FIG. 12 illustrates graphical views of experimental results from human eyes, according to an embodiment of the present invention.

As an example and demonstration of robustness of our method, FIG. 12 illustrates the successful detection of central fixation, with illumination of the upper indicator lights, in the 67-year-old presbyopic individual with essentially no remaining focusing ability and mild bilateral nuclear sclerotic cataracts who was measured through corrective lenses.

Polarization-modulated RBS provides unique advantages for eye-fixation detection. In contrast to the existing RBS technology, the approach described in this exemplary implementation employs just one photodetector per eye to measure a differential polarization signal. This simplifies both the optical and electronic design, with lower power consumption than conventional dual-photodetector RBS arrangements. This approach also eliminates most of the background noise associated with conventional RBS, typically improving the SNR by a factor of at least 100, and therefore avoids the need to perform an eyes-closed "background" measurement on each subject.

The polarization-modulated RBS approach, described herein, essentially achieves independence from binocular corneal birefringence. Preliminary attempts to minimize interference from corneal birefringence were made—a challenge faced by all polarization sensitive ophthalmic technologies—by incorporating a fixed wave plate in a monocular device, but results obtained using this "wave-plate-enhanced" approach were not independent of right- and left-eye corneal birefringence. The variable that was minimized in the optimization algorithm to find a solution that achieves maximal signal strength with the least variability across corneal birefringences was the normalized standard deviation (SD/mean) of RBS signal strengths. The minimized value for the polarization-modulated approach was (SD/mean=0.019, considering the central fixation frequencies only), which is about 15 times better than that of the older approach without the spinning HWP (SD/mean=0.287).

In contrast to existing eye-tracking and fixation-monitoring technologies, which measure external eye features whose location is neither constant relative to the fovea nor from one eye to the next, the radial pattern of Henle fiber birefringence (that the method of the present invention relies upon) defines the location of the fovea, and therefore the method of the present invention can detect fixation on a specified point not only directly (that is, without the need for individual calibration or separate background measurements), but also accurately, within ±0.75°. It should be noted that this measure of accuracy was derived from the full width at the half-maximum of the spatially-mapped distribution of the indicator of foveal fixation, which was taken as the preliminary threshold setting. Future studies in more subjects will show whether this threshold can be set higher, yielding even better accuracy.

The high uniformity and symmetry of the radial Henle fiber pattern which defines the fovea across eyes, independent of changes in external conditions and head motion, makes the approach of the present invention also more robust, and in principle allows fixation detection in any eye with a fovea. The major source of inter-subject variability associated with previous RBS technology, corneal birefringence, is essentially eliminated in the polarization-modulated approach, and variations in pupil size, refractive error, and fundus reflectivity are at least partially compensated for by normalization using the spinning artifact signal. A study on robustness of an existing remote eye-tracking system, with a reported ideal accuracy of at least ±1°, noted that 63% of individuals could not be tracked.

In the exemplary implementation it was demonstrated that polarization-modulated RBS allows foveal fixation detection in eyes with mild media opacities and through corrective lenses. Because no calibration measurement is necessary, studies are also possible with less cooperative subjects, such as young children who are at risk for disorders for which eye-fixation abnormalities are early indicators.

For example, polarization-modulated RBS has the potential to screen infants and youngsters reliably and directly for strabismus (a misalignment of the eyes in which only one eye fixates on a target at a time), which is the most common cause of amblyopia (lazy eye), before it becomes clinically apparent. Amblyopia is the leading medical cause of decreased vision in childhood. The early and accurate detection of even small eye-fixation deviations (at least 0.75° or approximately 1.5 prism diopters) that is permitted by the method of the present invention exceeds what is otherwise possible clinically (2-3 prism diopters) and would provide the opportunity to intervene optically (e.g., corrective eyeglasses or contact lenses) at an early stage and reduce or eliminate the need for subsequent strabismus surgery. In addition, early detection in such patients could enable the maintenance of high-grade binocularity, which is usually irretrievably lost from delays in diagnosis. Combining binocular polarization-modulated RBS with double-pass focus detection in the same optical pathway (via substituting a bull's eye focus detector for the RBS photodetector for each eye, conjugate to the original point source of light, to assess the size of the double-pass blur patch), can provide a robust and sensitive technique to screen young children automatically and reliably for both of the primary causes of amblyopia: strabismus and defocus.

Polarization-modulated RBS also has the potential to monitor eye fixation during visual field testing, laser eye surgery, optical coherence tomography, and other forms of diagnostic and therapeutic ophthalmic procedures.

Eye-fixation abnormalities have also been associated with a number of other medical conditions, such as autism and attention-deficit hyperactivity disorder (ADHD). The accurate monitoring of characteristic fixation abnormalities, as well as small and otherwise imperceptible errors of fixation, offers the potential not only to improve diagnosis, but also to monitor progress objectively, and to guide interventional strategies.

Finally, polarization-modulated RBS may enable new forms of human/machine interaction that rely on accurate, remote, eye-fixation-evoked machine control. For example, an array of emitter-sensor modules integrated into a display could allow selection of icons or keys through visual fixation only. Such interfaces could serve as a communication aid for individuals otherwise disabled or with limited mobility.

In short, this invention allows for a polarization-modulated approach to RBS that enables direct and reliable detection of true foveal fixation, without the need for individual calibration measurements or separate background measurements, and with large exit pupils facilitating simultaneous binocular testing with hand-held instruments. Preliminary results in human eyes demonstrate accuracies of at least ±0.75°. Polarization-modulated RBS has important implications and immediate practical relevance in a variety of disciplines, ranging from medical research and diagnostics to human/machine interaction.

The embodiments of the present invention described herein can variously use visible light, ultraviolet light, or infrared light, provided that the optical media of the eye are relatively transparent to the wavelength of light used. In addition, the embodiments of the present invention involve the use of polarized incident light. Although polarized incident light produced by an infrared laser diode is predominantly used in the various embodiments of the present invention, it would be obvious to one skilled in the art that other sources of polarized light could be used. For example, other lasers with necessary polarizers may be used to obtain the proper type of polarized light. Furthermore, other light sources may also be used for some applications, including incandescent light sources, light-emitting diodes, superluminescent diodes, and arc lamp sources. The use of other light sources presupposes the use of necessary filters to isolate certain wavelength bands of light and necessary polarizers to provide the proper type of polarization.

It will also be obvious to one skilled in the art that numerous opto-mechanical modifications of the embodiments described herein continue to fall within the scope of the present invention. For example, various types of polarimeters known to the art can be substituted for the polarization-sensitive detectors illustrated here. Sophisticated opto-mechanical scanning systems may be used in place of the spinning mirror scanning methods illustrated here. Integrated opto-electronic elements can combine emitters, beam splitters, and photodetectors into single compact assemblies. Objects other than the light sources and fixation marks of the illustrated embodiments may be used to advantage, particularly when the intended direction of fixation is in the center of a circularly scanned spot of light. Such objects can be flashed or otherwise modulated to attract attention. Annular areas of retina that are scanned may subtend visual angles smaller than, or larger than, 3 degrees. The eye fixation monitor embodiments illustrated here can also be conveniently combined with focus detecting optical systems, often sharing common optical elements, such that proper focus and proper fixation of the eye can be assessed simultaneously.

It will be understood by those with skill in the art that the polarization-related changes recorded in the process of eye fixation monitoring can provide valuable information regarding the presence or progression of various forms of eye disease or aging processes that affect the fovea or other retinal areas.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus for detecting fixation in at least one eye of a subject on a target comprising:
   a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein said optical illumination system further comprises a polarization modulating assembly configured to modulate the polarization of said illuminating beam;
   b) an optical detection system capable of detecting at least a portion of the illuminating beam of light of a) after being reflected back from the retina to provide a detection signal;
   c) a signal processing system adapted to communicate with the optical detection system to receive the detection signal;
   d) a signal analysis system adapted to communicate with the signal processing system to analyze the detection signal;
      wherein said polarization modulating assembly includes a thin-film-deposition optical element disposed at an oblique angle of incidence to said illuminating beam of light, said thin-film-deposition optical element gaining retardance from said tilted disposition and serving as a wave plate having fixed retardance capable of being varied by design of the characteristics of its deposited thin films to optimize said detection signal;
      wherein the detection signal of b) has a first frequency signature when said subject's eye is fixed on said target, and a second frequency signature when said subject's eye is not fixed on said target; and
      wherein a combination of said first and second frequency signatures is used to assess the fixation state of said subject's eye.

2. The apparatus of claim 1 wherein said thin-film-deposition optical element is tilted at an oblique angle of an amount included within the range from 15 to 75 degrees from perpendicular to the optical axis of said apparatus; thereby efficiently reflecting non-wanted back reflections of the beam of light away from the apparatus to avoid contamination of the signal detected by said optical detection system.

3. The apparatus according to claim 1 wherein said thin-film-deposition optical element comprises a combined dichroic beam splitter/retarder having the additional function of reflecting a visible light target onto the optical axis of said apparatus for intended fixation by said eye.

4. An apparatus for detecting fixation in at least one eye of a subject on a target comprising:
   a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein said optical illumination system further comprises a polarization modulating assembly including a spinning wave plate and a fixed wave plate configured to modulate the polarization of said illuminating beam;
   b) an optical detection system capable of detecting at least a portion of the illuminating beam of light of a) after being reflected back from the retina to provide a detection signal;
   c) a signal processing system adapted to communicate with the optical detection system to receive the detection signal;
   d) a signal analysis system adapted to communicate with the signal processing system to analyze the detection signal;
      wherein the detection signal of b) provides a first frequency signature when the subject's eye is fixed on said target, and provides a second frequency signature when the subject's eye is not fixed on said target, and a third frequency signature whenever the subject's eye is present and is reflecting light back into the detection system, and the third frequency signature is substantially independent of the fixation or non-fixation state of said subject's eye on said target; and
      wherein a combination of first and second frequency signatures is used to assess the fixation state of said subject's eye; and
      wherein said third frequency signature is primarily a function of fundus reflectivity, refractive error, pupil size, and clarity of the ocular optical media, and is substantially independent of corneal birefringence of the subject's eye via choice of the type of manipulation and modulation of the polarization of said illuminating beam, and is thereby capable of being used to normalize the strengths of said frequency signatures assessing the fixation state of said subject's eye.

5. The apparatus according to claim 4, wherein said optical illumination system comprises a scanning assembly configured to scan said illuminating beam in a cyclical spatial pattern on said portion of said retina at a scanning frequency.

6. The apparatus according to claim 4, wherein said first frequency signature comprises at least one frequency component that is directly proportional to said scanning frequency by a first proportionality constant and said second frequency signature comprises at least one frequency component that is directly proportional to said scanning frequency by a second proportionality constant, and said third frequency signature comprises at least one frequency component that is directly proportional to said scanning frequency by a third proportionality constant, wherein said first proportionality constant has a different value from a value of said second proportionality constant and from a value of said third proportionality constant.

7. The apparatus according to claim 4, wherein said polarization modulation frequency is selected relative to said scanning frequency to allow at least partial cancellation of optical noise in said optical detection system.

8. The apparatus according to claim 4, wherein the substructures of the portion of the retina of the eye scanned of a) comprise Henle fibers surrounding a fovea of the eye.

9. An apparatus for detecting focus condition of at least one eye of a subject on a target, comprising:
   a) an optical illumination system capable of scanning at least a portion of a retina of an eye of a subject with an illuminating beam of light, wherein the illuminating beam of light is polarized such that reflected portions of the illuminating beam are affected by birefringence of substructures of the retina, and wherein said optical illumination system further comprises a polarization modulating assembly configured to modulate the polarization of said illuminating beam;
   b) an optical detection system capable of detecting at least a portion of the illuminating beam of light of a) after being reflected back from the retina to provide a detection signal;
   c) a signal processing system adapted to communicate with the optical detection system to receive the detection signal;
   d) a signal analysis system adapted to communicate with the signal processing system to analyze the detection signal;
      wherein the detection signal of b) provides a first frequency signature when the subject's eye is fixed on said target, and provides a second frequency signature when the subject's eye is not fixed on said target, and a third frequency signature whenever the subject's eye is present and is reflecting light back into the detection system, and the third frequency signature is substantially independent of the fixation or non-fixation state of said subject's eye on said target; and
      wherein said third frequency signature is substantially independent of the corneal birefringence of said subject's eye via choice of the type of manipulation and modulation of the polarization of said illuminating beam; and
      wherein said third frequency signature is used to assess the goodness of focus of the eye.

10. The apparatus according to claim 9, wherein said optical illumination system comprises a scanning assembly configured to scan said illuminating beam in a cyclical spatial pattern on said portion of said retina at a scanning frequency.

11. The apparatus according to claim 9, wherein said first frequency signature comprises at least one frequency component that is directly proportional to said scanning frequency by a first proportionality constant and said second frequency signature comprises at least one frequency component that is directly proportional to said scanning frequency by a second proportionality constant, and said third frequency signature comprises at least one frequency component that is directly proportional to said scanning frequency by a third proportionality constant, wherein said first proportionality constant has a different value from a value of said second proportionality constant and from a value of said third proportionality constant.

12. The apparatus according to claim 9, wherein said polarization modulation frequency is selected relative to said scanning frequency to allow at least partial cancellation of optical noise in said optical detection system.

13. The apparatus according to claim 9, wherein said substructures of said portion of said retina of said subject's eye scanned comprise Henle fibers surrounding a fovea of said subject's eye.

14. The apparatus according to claim 9 wherein the first frequency signature includes frequencies approximately 2.5 and 6.5 times the scanning frequency.

15. The apparatus according to claim 9 wherein the second frequency signature includes frequencies approximately 3.5 and 5.5 times the scanning frequency.

16. The apparatus according to claim 9 wherein the third frequency signature is a frequency approximately 4.5 times the scanning frequency.

17. An apparatus for detecting fixation by an eye of a subject on a target comprising:
   a source of a polarized illuminating beam of light;
   a polarizing beam splitter positioned such that a linearly polarized beam of light emitted from the source of the polarized illuminating beam of light is reflected by the polarizing beam splitter along an optical axis in a direction of the eye of the subject;
   a scanner configured to create a circular scan on a retina of the eye of the subject with the polarized beam of light, wherein the polarized beam of light traverses retinal birefringent structures twice as it is reflected back toward the scanner, such that the scanner reflects the return beam of light back to the polarizing beam splitter; and
   a photodetector;
   wherein the return light is separated by the polarizing beam splitter into two orthogonally polarized components, such that a first polarized component is transmitted to the photodetector, and a second polarized component is reflected back to the source of the polarized illuminating beam of light; and
   a half wave plate configured to rotate at a predetermined frequency, and being disposed between the polarizing beam splitter and the scanner; and
   a non-rotating retarder tilted at an oblique angle to said optical axis and disposed between the half wave plate and the eye;
   wherein the retardance of said non-rotating retarder is chosen, in combination with the speed of rotation of the half wave plate, to manipulate and modulate the polarization of the beams of light double-passing through them such that the polarization changes induced by said retinal birefringent structures are detected optimally by said photodetector.

18. The apparatus of claim 17 wherein said non-rotating retarder comprises a beam splitter/retarder achieving its retardance via tilting of its deposited thin-film coatings.

19. The apparatus according to claim 18 wherein said beam splitter/retarder comprises a dichroic beam splitter having the additional function of reflecting a visible light target onto said optical axis for intended fixation by said eye.

20. The apparatus according to claim 17 wherein said non-rotating retarder is tilted at an oblique angle of an amount included within the range from 15 to 75 degrees from perpendicular to said optical axis; thereby efficiently reflecting non-wanted back reflections of the beam of light away from the apparatus to avoid contamination of the signal detected by the photodetector.

21. A method for detecting fixation in an eye of a subject on a target comprising:
scanning at least a portion of a retina of an eye of a subject with an illuminating beam of light, wherein the illuminating beam of light is polarized such that reflected portions of the illuminating beam are affected by birefringence of substructures of the retina;
modulating the polarization of said illuminating beam;
detecting at least a portion of the illuminating beam of light after being reflected back from the retina to provide a detection signal;
detecting a first frequency signature when the subject's eye is fixed on said target;
detecting a second frequency signature when the subject's eye is not fixed on said target;
detecting a third frequency signature whenever the subject's eye is present and is reflecting light back into the detection system, wherein the third frequency signature is substantially independent of the fixation or non-fixation state of said subject's eye on said target, and wherein the third frequency signature is substantially independent of corneal birefringence via choice of the type of manipulation and modulation of the polarization of said illuminating beam;
using a combination of first and second frequency signatures to assess the fixation state of said subject's eye; and
using the third frequency signature, wherein said third frequency signature is primarily a function of fundus reflectivity, refractive error, pupil size, and clarity of the ocular optical media, to normalize the strengths of said frequency signatures assessing the fixation state of said subject's eye.

22. A method for detecting focus condition of at least one eye of a subject on a target, comprising:
scanning at least a portion of a retina of an eye of a subject with an illuminating beam of light, wherein the illuminating beam of light is polarized such that reflected portions of the illuminating beam are affected by birefringence of substructures of the retina;
modulating the polarization of said illuminating beam;
detecting at least a portion of the illuminating beam of light after being reflected back from the retina to provide a detection signal;
detecting a first frequency signature when the subject's eye is fixed on said target;
detecting a second frequency signature when the subject's eye is not fixed on said target;
detecting a third frequency signature whenever the subject's eye is present and is reflecting light back into the detection system, wherein the third frequency signature is substantially independent of the fixation or non-fixation state of said subject's eye on said target, and wherein the third frequency signature is substantially independent of corneal birefringence via choice of the type of modulation of the polarization of said illuminating beam; and
using the third frequency signature to assess the goodness of focus of the eye.

23. An apparatus for detecting fixation by an eye of a subject on a target comprising:
a source of a polarized illuminating beam of light;
a non-polarizing beam splitter positioned such that a linearly polarized beam of light emitted from the source of the polarized illuminating beam of light is reflected by the non-polarizing beam splitter along an optical axis in a direction of the eye of the subject;
a scanner configured to create a circular scan on a retina of the eye of the subject with the polarized beam of light, wherein the polarized beam of light traverses retinal birefringent structures twice as it is reflected back toward the scanner, such that the scanner reflects the return beam of light back to the polarizing beam splitter; and
a dual-photodetector differential polarization detector;
wherein the return light is transmitted to the dual-photodetector differential polarization detector; and
a half wave plate configured to rotate at a predetermined frequency, and being disposed between the polarizing beam splitter and the scanner; and
a non-rotating retarder tilted at an oblique angle to said optical axis and disposed between the half wave plate and the eye;
wherein the retardance of said non-rotating retarder is chosen, in combination with the speed of rotation of the half wave plate, to manipulate and modulate the polarization of the beams of light double-passing through them such that the polarization changes induced by said retinal birefringent structures are detected optimally by said photodetector.

24. The apparatus of claim 23 wherein said non-rotating retarder comprises a beam splitter/retarder achieving its retardance via tilting of its deposited thin-film coatings.

25. The apparatus according to claim 23 wherein said beam splitter/retarder comprises a dichroic beam splitter having the additional function of reflecting a visible light target onto said optical axis for intended fixation by said eye.

26. The apparatus of claim 23 wherein said non-rotating retarder is tilted at an oblique angle of an amount included within the range from 15 to 75 degrees from perpendicular to said optical axis; thereby efficiently reflecting non-wanted back reflections of the beam of light away from the apparatus to avoid contamination of the signal detected by the photodetector.

* * * * *